(12) United States Patent
Tabibzadeh et al.

(10) Patent No.: US 8,106,001 B2
(45) Date of Patent: Jan. 31, 2012

(54) DIAGNOSTIC MARKERS OF HUMAN FEMALE INFERTILITY

(75) Inventors: Siamak Tabibzadeh, Albertson, NY (US); Ravi Kothapalli, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 291 days.

(21) Appl. No.: 11/796,404

(22) Filed: Apr. 27, 2007

(65) Prior Publication Data

US 2008/0200379 A1    Aug. 21, 2008

Related U.S. Application Data

(63) Continuation of application No. 09/674,254, filed as application No. PCT/US99/09366 on Apr. 29, 1999, now Pat. No. 7,211,644, said application No. 09/674,254 is a continuation-in-part of application No. 08/919,421, filed on Aug. 27, 1997, now Pat. No. 5,916,751.

(60) Provisional application No. 60/025,800, filed on Aug. 27, 1996, provisional application No. 60/083,418, filed on Apr. 29, 1998.

(51) Int. Cl.
*A61K 38/16* (2006.01)

(52) U.S. Cl. .............. 514/1.1; 514/8.9; 514/9.8

(58) Field of Classification Search .......... None
See application file for complete search history.

(56) References Cited

U.S. PATENT DOCUMENTS

| | | | |
|---|---|---|---|
| 4,444,879 A | | 4/1984 | Foster et al. |
| 5,166,058 A | * | 11/1992 | Wang et al. ............... 435/69.1 |
| 5,286,624 A | | 2/1994 | Terashima et al. |
| 5,395,825 A | * | 3/1995 | Feinberg et al. ................ 514/21 |
| 5,420,016 A | | 5/1995 | Boguslaski et al. |
| 5,554,339 A | | 9/1996 | Cozzette et al. |
| 5,616,561 A | | 4/1997 | Barcellos-Hoff |
| 5,631,142 A | * | 5/1997 | Wang et al. ................ 435/69.1 |
| 5,693,479 A | * | 12/1997 | Feinberg et al. ............ 435/7.21 |
| 5,709,837 A | | 1/1998 | Mori et al. |
| 5,874,479 A | | 2/1999 | Martin |
| 5,885,794 A | * | 3/1999 | Mathews et al. ................ 506/4 |
| 5,916,751 A | | 6/1999 | Tabibzadeh et al. |

(Continued)

FOREIGN PATENT DOCUMENTS

WO    94/20637    *    9/1994

(Continued)

OTHER PUBLICATIONS

Swiss-Prot Accession No. O00292, human EBAF, also known as Lefty2, TGFB-4.*

(Continued)

*Primary Examiner* — Albert Navarro
*Assistant Examiner* — Ginny Portner
(74) *Attorney, Agent, or Firm* — Saliwanchik, Lloyd & Eisenschenk

(57) ABSTRACT

The subject invention pertains to methods and reagents for the diagnosis of female infertility, prognostic indicators for female infertility, compounds for the treatment of female infertility, compounds and methods for contraception. Methods and compounds are based on the levels of ebaf in endometrial tissue. Methods for diagnosing endometrial receptivity and bleeding function by screening a biological sample such as an endometrial tissue sample, or bodily fluid for the presence of ebaf. A contraceptive compound containing an effective amount of ebaf and a pharmaceutically acceptable carrier. A diagnostic kit for timing contraception containing reagents for screening a sample for the presence of ebaf. A method of treating endometrial irregularities by down-regulating the expression of ebaf.

13 Claims, 12 Drawing Sheets

U.S. PATENT DOCUMENTS

| | | | |
|---|---|---|---|
| 6,027,917 | A | 2/2000 | Celeste et al. |
| 6,040,431 | A | 3/2000 | Keck et al. |
| 6,242,568 | B1 | 6/2001 | Barbas et al |
| 6,294,662 | B1 | 9/2001 | Tabibzadeh |
| 6,428,966 | B1 * | 8/2002 | Lee et al. ............... 435/7.1 |
| 6,440,445 | B1 * | 8/2002 | Nowak et al. ............ 424/423 |
| 6,492,497 | B1 | 12/2002 | Thompson et al. |
| 6,635,480 | B1 * | 10/2003 | Lee et al. ............... 435/325 |
| 6,649,588 | B1 | 11/2003 | Tabibzadeh et al. |
| 6,677,432 | B1 | 1/2004 | Oppermann et al. |
| 6,683,156 | B1 * | 1/2004 | Tabibzadeh ............ 530/350 |
| 6,747,004 | B1 | 6/2004 | Tabibzadeh |
| 7,204,978 | B1 * | 4/2007 | Robertson et al. ......... 424/85.1 |
| 7,270,963 | B2 * | 9/2007 | Lee et al. ............... 435/7.1 |
| 2002/0086351 | A1 * | 7/2002 | Ebner et al. ............ 435/69.1 |
| 2002/0146414 | A1 * | 10/2002 | Sakiyama-Elbert et al. ............ 424/141.1 |
| 2002/0169292 | A1 * | 11/2002 | Weintraub et al. ......... 530/397 |
| 2003/0022841 | A1 * | 1/2003 | Lee et al. ............... 514/12 |
| 2003/0032047 | A1 | 2/2003 | Tabibzadeh |
| 2003/0064069 | A1 | 4/2003 | Thompson et al. |
| 2003/0091566 | A1 | 5/2003 | Thompson et al. |
| 2003/0158379 | A1 * | 8/2003 | Celeste et al. ............ 530/350 |
| 2004/0146891 | A1 * | 7/2004 | Lee et al. ............... 435/6 |
| 2005/0095592 | A1 * | 5/2005 | Jazaeri et al. ............ 435/6 |
| 2005/0276802 | A1 | 12/2005 | Adams et al. |
| 2008/0242604 | A1 * | 10/2008 | Ebner et al. ............ 514/12 |

FOREIGN PATENT DOCUMENTS

| | | | |
|---|---|---|---|
| WO | 96/05857 | * | 2/1996 |
| WO | 96/21427 | * | 7/1996 |
| WO | 98/39021 | * | 9/1998 |
| WO | WO 99/06443 | | 2/1999 |
| WO | WO 99/06444 | | 2/1999 |
| WO | WO 99/55902 | | 11/1999 |
| WO | 00/64481 | * | 11/2000 |
| WO | WO 01/01134 | | 1/2001 |

OTHER PUBLICATIONS

Swiss-Prot accession No. O 00292.*

RNA Image Kit Product Brochure, 1993, pp. 1-21.

"DNA Sequencing by the Dideoxy Method," Sequences Ver. 2.0 A New Genetically Engineered Enzyme for DNA Sequencing, U.S. Biochemical Corp., 1988-89, pp. 7-29-7-35.

Analysis of RNA by Northern and Slot Blot Hybridization, Current Protocols in Molecular Biology, Unit 4.9, 1993, pp. 4.9.1-4.9.14.

Hillier et al. Genbank Accession No. R37562, May 1995.

Frigerio et al. Genbank Accession No. T25016, May 1995.

Liang et al. "Differential Display Using One-Base Anchored Oligo-dT Primers" *Nucleic Acids Research*, 1994, pp. 5763-5764, vol. 22, No. 25.

Tabibzadeh et al. "Distinct Tumor Specific Expression of TGFB4 (ebaf), a Novel Human Gene of the TGF-B Superfamily" *Frontiers in Bioscience 2*, Jul. 1997, pp. 18-25.

Tabibzadeh et al. "Dysregulated Expression of ebaf, a Novel Molecular Defect in the Endometria of Patients with Infertility" *The Journal of Clinical Endocrinology & Metabolism*, Mar. 8, 2000, pp. 2526-2536, vol. 85, No. 7.

Tabibzadeh et al. "Temporal and Site-Specific Expression of Transforming Growth Factor-β4 in Human Endometrium" *Molecular Human Reproduction*, 1998, pp. 595-602, vol. 4, No. 6.

http://users.rcn.com/jkimball.ma.ultranet/BiologyPages/R/Radioimmunoassay.html.

Capecchi, M.R., "Altering the Genome by Homologous Recombination" *Science*, 1989, pp. 1288-1292, vol. 244, No. 4910.

Davies, N.P., et al. "Targeted alterations in yeast artificial chromosomes for inter-species gene transfer" *Nucleic Acids Research*, 1992, pp. 2693-2698, vol. 20, No. 11.

Huxley, C., et al. "The Human HPRT Gene on a Yeast Artificial Chromosome is Functional When Transferred to Mouse Cells by Cell Fusion" *Genomics*, 1991, pp. 742-750, vol. 9.

Jakobovits, A., et al., "Germ-line transmission and expression of a human-derived yeast artificial chromosome" *Nature*, Mar. 18, 1993, pp. 255-261, vol. 362.

Johnson, S. and Bird, R.E., "Construction of Single-Chain Fv Derivatives of Monoclonal Antibodies and Their Production in *Escherichia coli*" *Methods in Enzymology*, 1991, pp. 88-99, vol. 203, JJ Langone ed.; Academic Press, New York, NY.

Lamb, B.T., et al., "Introduction and expression of the 400 kilobase *precursor amyloid protein* gene in transgenic mice" *Nature Genetics*, Sep. 1993, pp. 22-29, vol. 5.

Pearson, B.E. and Choi, T.K., "Expression of the human β-amyloid precursor protein gene from a yeast artificial chromosome in transgenic mice" *Proceedings of the National Academy of Sciences USA*, Nov. 1993, pp. 10578-10582, vol. 90.

Rothstein, R., "Targeting, Disruption, Replacement, and Allele Rescue: Integrative DNA Transformation in Yeast" *Methods in Enzymology* 1991, pp. 281-301, vol. 194, Chapter 19, Guide to Yeast Genetics and Molecular Biology, eds. C. Guthrie and G. Fink, Academic Press, Inc.

Schedl, A., et al., "A yeast artificial chromosome covering the tyrosinase gene confers copy number-dependent expression in transgenic mice" *Nature*, Mar. 18, 1993, pp. 258-261, vol. 362.

Strauss, W.M., et al., "Germ Line Transmission of a Yeast Artificial Chromosome Spanning the Murine $a_1$ (I) Collagen Locus" *Science*, Mar. 26, 1993, pp. 1904-1907, vol. 259, No. 5103.

Gruidl, M., et al., "The progressive rise in the expression of α crystalline B chain in human endometrium is initiated during the implantation window: modulation of gene expression by steroid hormones" *Molecular Human Reproduction*, 1997, pp. 333-342, vol. 3, No. 4.

Lessey, B.A., et al., "Integrin Adhesion Molecules in the Human Edometrium, Correlation with the Normal and Abnormal Menstrual Cycle" *The Journal of Clinical Investigation*, Jul. 1992, pp. 188-195, Vo. 90.

Kumar, S., et al., "Progesterone Induces Calcitonin Gene Expression in Human Endomentrium within the Putative Window of Implantation" *Journal of Clinical Endocrinology and Metabolism*, 1998, pp. 4443-4450, vol. 83, No. 12.

Molloy, S.S., et al., "Bi-cycling the furin pathway: from TGN localization to pathogen activation and embryogenesis" *Trends in Cell Biology*, Jan. 1999, pp. 28-35, vol. 9.

Kothapalli, Ravi et al., *Journal of Clinical Investigation*, May 1997, pp. 2342-2350, vol. 99, No. 10.

Leonard, S.N., et al., "Transforming growth factor beta 1 expression in the endometrium of the mare during placentation" *Molecular Reproduction and Development*, 1995, pp. 131-140, vol. 42.

Wieczorek, Z., et al, "The immunomodulatory diversity of the proteins of the transforming growth B (TGFB) family" *International Journal of Peptide and Protein Research*, Jul. 1995, pp. 113-118, vol. 46.

Meno, Chikara, et al., "Left-right asymmetric expression of the TGFB-family member lefty in mouse embryos" *Nature*, May 9, 1996, vol. 381.

Burt, D.W., et al., "Multiple growth factor mRNAs are expressed in chicken adipocyte precursor cells" *Biochemical and Biophysical Research Communications*, Sep. 30, 1992, pp. 1298-1305, vol. 187, No. 3.

Bowie, James U., et al., "Deciphering the Message in Protein Sequences: Tolerance to amino acid substitution" *Science*, Mar. 16, 1990, pp. 1306-1310, vol. 247.

Bassi et al., Accession Nos. AF081508; AF081510; AF081509.

Meno, et al., *Nature* 1996, reference of record, 151-155.

Sporn, M.B., et al., "Cell Regulation" The American Society of Cell Biology, Nov. 1990, pp. 875-882.

Roberts, A.B., et al., Phil. Trans. R. Soc. Lond. B, 1990, pp. 145-154, vol. 327.

Burt, David W., et al., Molecular Endorcrinology, pp. 989-992, vol. 6, No. 6.

Flanders, Kathleen C., et al., "Antibodies to peptide determinants in Transforming Growth Factor B and their Applications" *Biochemistry* 1988, pp. 739-746, vol. 27.

Postlethwaite, A.E., et al., *Journal of Cellular Physiology*, 1995, pp. 587-592, vol. 164.

Teicher, B.A., et al., "Cancer Chemther" *Pharmacol* 1996, pp. 601-609, vol. 37.

Newcom, Samuel, R., et al., *Blood*, Jun. 15, 1990, pp. 2434-2437, vol. 75, No. 12.

Dillner, J., et al., "Antibodies Against a Synthetic Peptide (Gly-Ala)" *PNAS*, Aug. 1984, pp. 4652-4656, vol. 18.

Oosterlynck, D.J., et al., "Transforming growth factor B activity is increased in peritoneal fluid from women with endometriosis" Feb. 1994, pp. 287-292, vol. 83, No. 2.

Ayala, A., et al., "The release of transforming growth factor B following hemorrhage: its role as a mediator for host immunosuppression" *Immunology*, 1993, pp. 479-484, vol. 79.

Hoefer, M., et al., Anti (transforming growth factor B) antibodies with predefined specificity inhibit metastasis of highly tumorigenic human xenotransplants in nu/nu mice 1995, pp. 302-308, vol. 41.

* cited by examiner

DIAGNOSTIC MARKERS OF HUMAN FEMALE INFERTILITY

CROSS-REFERENCE TO RELATED APPLICATIONS

This application is continuation of U.S. Ser. No. 09/674,254, filed Dec. 27, 2000, now U.S. Pat. No. 7,211,644, which is the U.S. national stage application of International patent application No. PCT/US99/09366, filed Apr. 29, 1999, and claims the benefit under 35 USC §119(e) of U.S. provisional application Ser. No. 60/083,418, filed Apr. 29, 1998, and U.S. Ser. No. 09/674,254, filed Dec. 27, 2000, is a continuation-in-part of U.S. application Ser. No. 08/919,421, filed Aug. 27, 1997, now U.S. Pat. No. 5,916,751, which claims the benefit under 35 USC §119(e) of U.S. provisional application Ser. No. 60/025,800, filed Aug. 27, 1996.

GOVERNMENT SUPPORT

This invention was made with Government support under Grant Number (s) CA46866 awarded by the National Institutes of Health (NIH) and HD 35041 and HD 34824 from the National Cooperative Program on Markers of Uterine receptivity for Blastocyst Implantation. The Government has certain rights in the invention.

BACKGROUND OF THE INVENTION

1. Field of the Invention

The present invention relates to diagnostic and prognostic markers of endometrial irregularities, particularly infertility. More specifically, the present invention relates to diagnostic markers which can be used in treatment of infertility, kits for timing conception, contraception, and for treatment of excessive bleeding conditions.

2. Background Art

Human endometrium is a unique tissue that undergoes sequential phases of proliferation, secretory changes, tissue shedding and bleeding during menstruation. After ovulation, during a defined period designated as "period of endometrial receptivity" or "implantation window", a number of sequential changes at the structural and molecular levels make human endometrium susceptible to implantation (Tabibzadeh et al., 1995).

In humans, the ovum is fertilized in the Fallopian tube. The fertilized ovum starts to divide, migrates through the Fallopian tube and enters the uterine cavity around the $3^{rd}$ to $4^{th}$ day after ovulation. The blastocyst remains free floating within the endometrial cavity for a day and initiates implantation on day 5-10 after ovulation (Hertig et al., 1956; Formigli et al., 1987; Rogers et al., 1989; Navot et al., 1989; Navot et al., 1991). The identity of the members of the molecular repertoire that make the endometrium receptive to the implantation process still remains largely unknown. If implantation does not occur, however, a second series of changes lead to menstrual shedding of human endometrium. A member of this premenstrual molecular repertoire was recently identified (Kothapalli et al., 1997; Tabibzadeh et al., 1997). The expression of this novel gene was confined to the endometrium immediately prior to and during menstrual bleeding and hence it was originally designated as endometrial bleeding associated factor (ebaf) (Kothapalli et al., 1997). In fact, consistent with its intimate relation with endometrial bleeding, the expression of the gene was found in the endometrium during abnormal uterine bleeding (Kothapalli et al., 1997).

The deduced amino acid sequence of ebaf showed a great amount of identity and similarity with the known members of the TGF-β superfamily. A motif search revealed that the predicted ebaf protein contains most of the conserved cysteine residues of the TGF-β related proteins (Kothapalli et al., 1997) which are necessary for the formation of the cysteine knot structure (Kingsley, D. M., 1994; Daopin et al., 1992). The ebaf sequence contains an additional cysteine residue, 12 amino acids upstream from the first conserved cysteine residue. The only other TGF-β superfamily members, known to contain an additional cysteine residue, are TGF-βs, inhibins and GDF-3 (Kingsley, D. M., 1994; McPherron et al., 1993). ebaf, similar to lefty, GDF-3/Vgr2 and GDF-9, lacks the cysteine residue necessary for the formation of intermolecular disulfide bond (McDonald et al., 1993; McPherron et al., 1993; Jones et al., 1992). Additionally, whereas the carboxy terminus of the TGF-β family is usually CX1CX1, ebaf has a longer C terminal sequence, CX1CX19 (Meno et al., 1996). Therefore, ebaf appears to be an additional member of the TGF-β super family with an unpaired cysteine residue which may not exist as a dimer (Tabibzadeh et al., 1997).

A gene which is called lefty/stra3 of the TGF-β super family is expressed during development in the left side of the mouse embryo in the mesenchyme (Meno et al, 1996; Boullet et al., 1995). The deduced amino acid sequence of ebaf protein is 77% identical and 83% similar to lefty (Meno et al, 1996). Therefore, lefty may be the mouse homolog of the human ebaf or a closely related molecule (Kothapalli et al., 1997; Meno et al, 1996).

Implantation is a complex process which requires interaction of the blastocyst and subsequently the developing embryo and placenta with the endometrium. Initially during this process, blastocyst establishes contact with the surface epithelium of endometrium. Subsequently, during a series of exquisitely controlled steps, the blastocyst is gradually implanted in the underlying stroma. Formation of placenta, the so-called placentation completes the implantation process and establishes a means of supporting the embryo to the end of the pregnancy period.

Most of the information regarding the phases of human implantation are derived from the specimens available in the Carnegie collections. Based on this material, implantation has been divided into various stages (Table 1). At the stage 4a, trophoblasts in different species, use one of the following modes of invasion of endometrium (Schlafke and Enders, 1975):

1. Displacement penetration (mouse, rat): In this mode of endometrial invasion, surface epithelial cells detach from their basement membrane and from each other, they degenerate and then are phagocytozed by trophoblasts. As a consequence, process of implantation is initiated by the exposure of the trophoblasts to the bare underlying basement membrane.
2. Fusion penetration (rabbit, ruminants): In this type of implantation, sycytiotrophoblasts fuse with the surface epithelial cells and form a syncytium that penetrates the basement membrane of the surface epithelium.
3. Intrusion penetration (carnivores): In this type of implantation, the processes of the syncytiotrophoblasts penetrate between the surface epithelial cells and junctions are formed between the trophoblasts and the epithelial cells. The trophoblasts interposed among epithelial cells gradually penetrate through the underlying basement membrane of the surface epithelium.

Markers and Factors of Endometrial Receptivity

Two sets of factors, of endometrial and embryonic origins are required for the establishment of a dialogue between the implanting blastocyst and the receptive endometrium. Various experimental evidence have shown that endometrium is well prepared for the implantation during a defined period that is called the implantation window (Psychoyos 1973a, b, 1986, 1988, Psychoyos and Casimiri, 1980. This phase is followed by a non-receptive phase when the endometrium is refractory to the implantation process (Psychoyos, 1993, Strauss and Gurpide, 1991). However, there is no general agreement as to the dates and duration of such implantation window.

For example, it has been suggested that the implantation window is confined to the postovulatory days 5-7 of the normal menstrual cycle (Psychoyos, 1993). Rogers and Murphy concluded that the human implantation window must be at least 3.5 days (Rogers and Murphy, 1989) whereas Formigli et al suggested that the period of endometrial receptivity may be as long as 7 days (Formigli et al, 1987). In vitro fertilization (IVF) trials have also shown that there is a period of receptivity for the endometrium. For the 4-12 cell stage conceptus, the optimal period of transfer seems to be on days 17-19 of the artificial cycles with day 15 being the first day of administration of progesterone (Navot et al, 1991, Rosenwaks 1987). In some IVF trials, pregnancies were established when the conceptuses were transferred on days 16 to 19 but not on days 20-24 of the artificial cycles (Navot et al, 1986, Rosenwaks, 1987).

In one series of studies, it was concluded that the implantation took place between days 7 to 11 after embryo transfer (Tur-Kaspa et al, 1990). The timing of this transfer window seems to vary, depending on the developmental state of the transferred conceptus and the method of hormone treatment. The shorter duration for the embryo transfer in some artificially induced cycles may be attributable to the rapidity by which endometrium is prepared. For example, the date of endometrial biopsies were found to be more advanced than expected after induction of ovulation by HMG/HCG regimen (Garcia et al, 1984, Martel et al, 1987).

The endometrium becomes responsive to implantation during a defined period. A large number of factors have been described whose expression frames the putative implantation window. However, factors that are merely a hallmark of this phase should be clearly separated from those that truly participate in the implantation process and whose presence is required for a successful implantation. Mere expression of a given factor during the implantation window is not sufficient to identify a marker as being essential to the implantation process. Lack of expression of a bona fide implantation specific gene in humans should lead to infertility. On the other hand, lack of expression of such a factor or inhibition of its effect in animals should lead to implantation failure. In addition, the endometrial receptivity may not be solely dependent on expression of receptive marker(s), rather it may be due to simultaneous loss of signals inhibitory to implantation.

The fact that subsequent to the receptive phase, endometrium can act as a barrier to the implantation process is consistent with the hypothesis that endometrial factors that actively inhibit implantation may exist. In fact, removal of endometrium from the mouse uterus allows successful implantation of mouse blastocysts (Cosell, 1969).

In addition, implantation can be delayed by administration of progesterone. However, when the blastocysts are removed from the uterus of the animal treated with progesterone, they exhibit the ability to proliferate, to attach and to assume an invasive behavior similar to their normal counterparts. The delay in implantation induced by progesterone can be overcome by injection of estrogen or actinomycin D (Finn et al, 1973). Therefore, endometrium seems to possess factors that regulate or prevent the implantation process. It has been suggested that MUC-1, an integral membrane protein, may serve as one such barrier mechanism (Braga and Gendler, 1993). Other factors such as ebaf (Kothapalli et al, 1997) and BK66 (Lessing et al, 1996) may objectively define the closure of the implantation window and may be part of the repertoire that inhibits implantation.

In a substantial number of women, implantation fails to occur and these women do not become pregnant. As shown in the classic Guttmacher's table (Table 1), about 7% of couples can be considered infertile after they have tried for two years to attain pregnancy (Guttmacher, 1956). In the US, in 1982, nearly one in five married women of reproductive age reported that, during their lifetime, they had sought professional help for infertility (Mosher et al., 1991) and in 1988, 8.4% (a total of 4.9 million) of women, ages 15-44, reported impaired fecundity (Mosher et al., 1993). After all the standard clinical investigations are done and known causes of infertility attributable to tubal and pelvic pathologies, male factor, ovulatory dysfunction and unusual problems are ruled out, a substantial number (10%) of infertility cases remain of unknown etiology. These cases are designated as "unexplained infertility" (Speroff et al., 1994). Regardless of the cause, however, infertility may be associated with development of lesions within the molecular repertoire of endometrium during the critical "period of endometrial receptivity". For example, it was shown that infertility is associated with aberrant expression of the $a_v b_3$ which is normally present in endometrium during the "receptive phase" of the menstrual cycle (Lessey et al., 1992; Lessey et al. 1994). Such molecular lesions may be due to the inability of human endometrium to express the factors required for the receptivity of endometrium to implantation or alternatively may be due to dysregulated expression of the "premenstrual molecular repertoire" which renders the endometrium non-receptive to implantation (Tabibzadeh, 1996; Tabibzadeh, 1995).

It would therefore be useful to develop improved methods and reagents for the diagnosis of female infertility, prognostic indicators for female infertility, compounds for the treatment of female infertility, compounds and methods for contraception.

SUMMARY OF THE INVENTION

According to the present invention, methods and reagents for the diagnosis of female infertility, prognostic indicators for female infertility, compounds for the treatment of female infertility, compounds and methods for contraception are provided. The methods and compounds are based on the levels of ebaf in endometrial tissue. Provided are methods for diagnosing endometrial receptivity and bleeding functions by screening a biological sample such as an endometrial tissue sample, or bodily fluid for the presence of ebaf. A contraceptive compound containing an effective amount of ebaf and a pharmaceutically acceptable carrier is also provided. Additionally, a diagnostic kit for timing conception is provided, containing reagents for screening a sample for the presence of ebaf. Also provided is a method of treating endometrial irregularities by down-regulating the expression of ebaf.

BRIEF DESCRIPTION OF THE DRAWINGS

Other advantages of the present invention will be readily appreciated as the same becomes better understood by reference to the following detailed description when considered in connection with the accompanying drawings wherein:

FIG. 19A: in each lane, 10 micrograms of extracted endometrial proteins was resolved in a 15% gel by SDS-PAGE and then subjected to Western blot analysis; the blot was probed with the antiserum alone (left lane) and with the antiserum-preincubated with a 100 molar excess of the CASDGALVPRRLQHRP-amide (SEQ ID NO: 3); the antiserum was used at 1:250 dilution of a solution containing 0.8 mg protein/ml; the peptide was used at 0.32 mg/ml; several immunoreactive bands (55/60, ~41, ~33, ~25 kD) were detected by the antiserum (left lane); immunoreactivity of the antiserum markedly reduced by its pre-incubation with the peptide (right lane); FIG. 19B: 250 micrograms total protein from a menstrual day 1 endometrium was immunoprecipitated using the rabbit antiserum to ebaf; the detected proteins bands were similar in size to those identified by Western blotting; in addition, an additional, ~12 kD, band was also detected, the size of the proteins is shown in kilodalton;

DETAILED DESCRIPTION OF THE INVENTION

According to the present invention, methods and reagents for the diagnosis of female infertility, prognostic indicators for female infertility, compounds for the treatment of female infertility, and compounds and methods for contraception are provided. The methods and compounds are based on the role of ebaf in endometrial tissue. Provided are methods for diagnosing endometrial receptivity and bleeding functions by screening a biological sample such as an endometrial tissue sample, or bodily fluid for the presence of ebaf. A contraceptive compound containing an effective amount of ebaf and a pharmaceutically acceptable carrier is also provided. Additionally, a diagnostic kit for timing conception is provided, containing reagents for screening a sample for the presence of ebaf. Also provided is a method of treating endometrial irregularities by down-regulating the expression of Endometrial Bleeding Associated Factor (ebaf), previously known as Premenstrual Factor expressed by the pmf-1 gene. Ebaf also referred to at one time as TGF-β4 due to the similarity in sequence however it has subsequently been distinguished from TGF-β4.

Ebaf mRNA is normally expressed in the endometrium during the critical period when the endometrium is destined to be shed and it becomes refractory to implantation. Therefore, ebaf is regarded as a member of the premenstrual molecular repertoire and a marker for a non-receptive endometrium. The applicant examined the temporal expression of the ebaf mRNA and protein in normal human endometrial samples during the menstrual cycle and in endometrial samples of women with diverse forms of infertility during the implantation window. Applicants show that gene is aberrantly expressed in a subset of infertile women.

Figure 1:
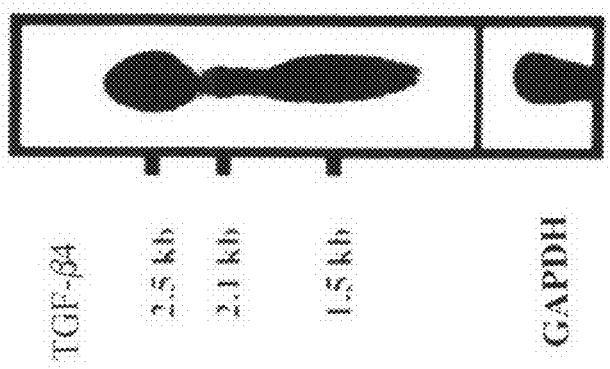
FIG. 1 is a photograph of a Northern blot of ebaf mRNA expression in menstrual endometria samples; 20 µg total RNA from four menstrual endometria was subjected to Northern blot analysis using the full length, placentally derived ebaf cDNA as the probe; the integrity of RNA was verified by staining the 18S and 28S ribosomal RNA (not shown) and hybridization of the blot with a cDNA probe to GAPDH (lower panel); the figure is representative of the data. At least three mRNA species of the ebaf in the size of 2.5, 2.1 and 1.5 kB are observed.

The applicant has shown by Northern blot analysis of ebaf mRNA expression in menstrual endometria samples that at least three mRNA species of ebaf in the size of 2.5, 2.1 and 1.5 kB are observed. The expression a 1.5 kB in the endometria of infertile women is not expressed in endometria of normal individuals. (FIG. 1). Infertility generally is associated with deregulated expression of the ebaf mRNA during the implantation window. More specifically the present invention provides for nucleic acid assays in which detection of the 1.5 kB mRNA species of ebaf is indicative of infertility. Treatment of an individual with ebaf, more specifically the 1.5 kB gene or the protein expressed by that gene are provided as a method of contraception. Removal of ebaf, for example by antisense treatment can restore fertility.

Figure 2:
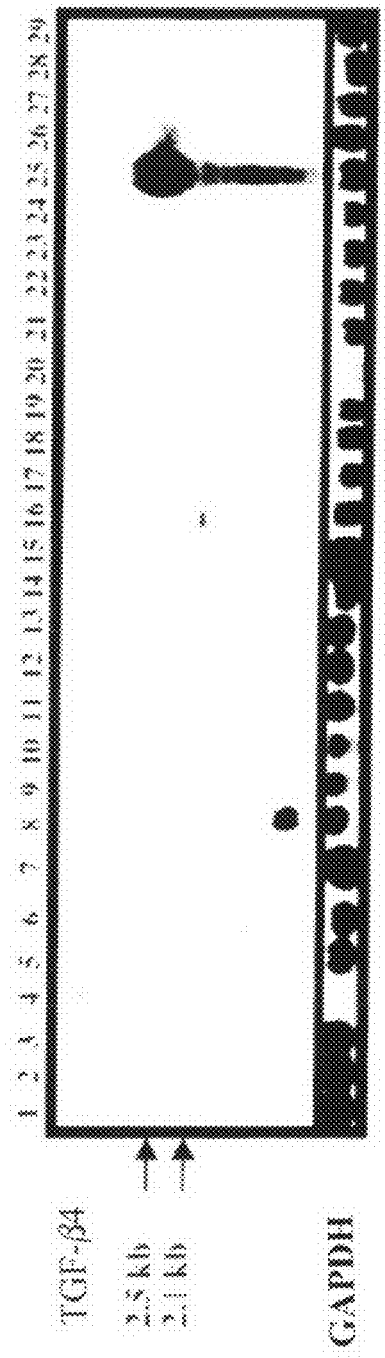
FIG. 2 is a photograph of a Northern blot of ebaf mRNA expression in endometria samples from fertile and infertile women; Upper panel: 20 µg total RNA from endometria samples of fertile and infertile women and a negative control (RNA from HL 60 cell line) were subjected to the Northern blot analysis using the full length ebaf cDNA as the probe; for lane legend see Table 3; the integrity of RNA was verified by staining the 18S and 28S ribosomal RNA (not shown) and hybridization of the blot with a cDNA probe to GAPDH (lower panel)

Reverse transcription polymerase chain reaction (rtPCR) followed by Southern blot analysis revealed various types of abnormal expression of ebaf mRNA that allow types of infertility to be differentiated from each other (FIG. 2). Northern blot analysis carried out on the endometria of patients with various types of infertility during the implantation window (Table 3) showed that in more than 50% of infertile patients, the ebaf mRNA was detectable in the endometria of women on the post-ovulatory days 6-10 (FIG. 2). The mRNA detected was primarily the 2.1 kb species. Additional smaller bands were also detected in a smaller number of patients (FIG. 2). A high incidence of dysregulated ebaf mRNA expression, however, was identified in women with endometriosis and with unexplained infertility (Table 3, FIG. 2).

In contrast, endometrium obtained a normal fertile woman (egg donor) during the implantation window, exhibited a low level of ebaf mRNA expression (FIG. 2, lane 21).

To localize ebaf protein in endometrial samples and samples of bodily fluids for similar purposes, the invention provides methods whereby polyclonal antisera is raised against ebaf or a synthetic peptide provided by the invention, CASDGALVPRRLQHRP-amide (SEQ ID NO:3). The antisera preferably are pooled and affinity purified on a column with the peptide bound. Similarly monoclonal antibodies could be used as is well known in the art.

Figure 3:
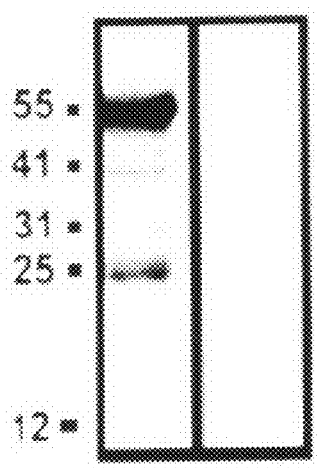
FIG. 3 is a photograph demonstrating the specificity of rabbit antiserum to ebaf by Western blot analysis; in each lane, 10 µg of extracted endometrial proteins was resolved in a 15% gel by SDS-PAGE and then subjected to Western blot analysis; the blot was probed with the antiserum alone (left lane) and with the antiserum-preincubated with a 100 molar excess of the CASDGALVPRRLQHRP-amide (SEQ ID NO: 3); the antiserum was used at 1:250 dilution of a solution containing 0.8 mg protein/ml; the peptide was used at 0.32 mg/ml; for lane legend see Table 1; several immunoreactive bands (55/60, 41, 31, 25 kD) were detected by the antiserum (left lane); the immunoreactivity of the antiserum markedly reduced by the pre-incubation with the peptide (right lane); the size of the proteins are shown in kilodaltons.
Figure 4:
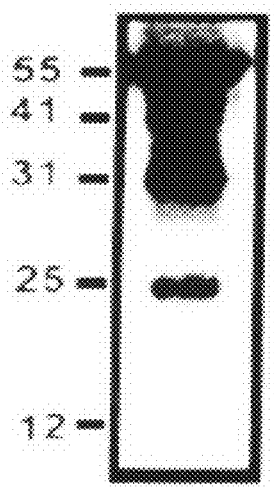
FIG. 4 is a photograph demonstrating the immunoreactive ebaf bands by immunoprecipitation Western blot analysis; 250 µg total protein from a menstrual day 1 endometrium sample was immunoprecipitated using rabbit antiserum to ebaf; the detected proteins bands were similar in size to those identified by Western blotting (FIG. 3); in addition, an additional 12 kD band was also detected; the size of the proteins are shown in kilodaltons.

Various forms of ebaf protein in endometrial samples, endometrial fluid and serum during the menstrual cycle can be detected. The size of the ebaf precursor protein is 41 kD. However, ebaf protein contains three RXXR cleavage sites which conform to the minimal requirement for efficient processing by Furin, a ubiquitous prototypical mammalian kexin/subtilisin-like endoproteinase involved in the proteolytic processing of a variety of proteins including those within the ebaf super family. If all these sites are cleaved, then products of the molecular weights of 32.3, 25.7 and 12 kD proteins are expected to be secreted (Table 2). To detect such proteins in endometrial samples, fluids and serum the CASDGALVPRRLQHRP-amide antisera is used. In endometrial samples the antisera detects ebaf bands at 55/60, 41, 31, 25 kD by Western blot analysis. The relative optical densities of these bands were significantly greater during the late secretory phase as compared to the proliferative phase (FIG. 3). However, the predicted 12 kD protein was not detected. Endometrial proteins, immuno-precipitated by the antiserum and to SDS-PAGE and examined by Western blot analysis revealed the additional 12 kD protein band (FIG. 4).

Figure 5:
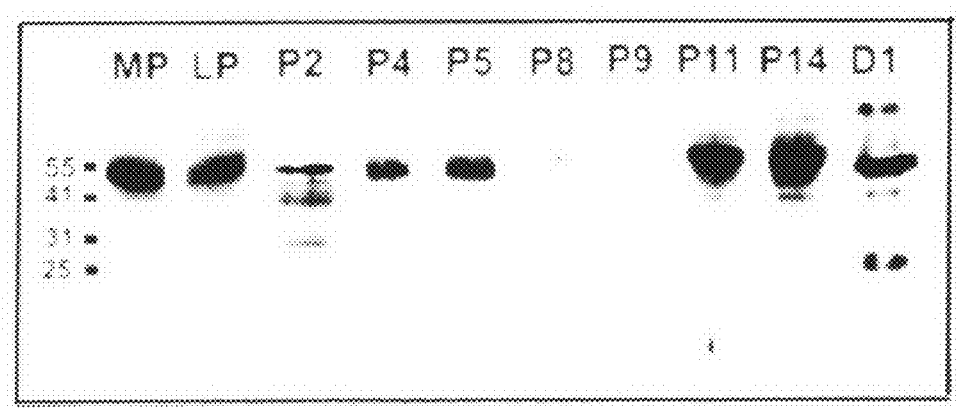
FIG. 5 is a photograph showing the immunoreactive ebaf bands in endometria samples throughout the menstrual cycle; in each lane, 10 µg of extracted endometrial proteins was resolved in a 15% gel by SDS-PAGE and then subjected to Western blot analysis; the blot was probed with the affinity purified rabbit antiserum to ebaf; the antiserum reacts with the protein bands in the size of 55/60, 41, 31, and 25 kD; the immunoreactivity of the bands is markedly reduced in endometrial samples obtained on the post-ovulatory day 4, 5, 8 and 9; MP: mid-proliferative, LP: late proliferative, P: post-ovulatory day, D1: first day of menstruation; the size of the proteins are shown in kilodaltons.

Applicant's investigation of the immunoreactive ebaf bands in endometrial samples throughout the menstrual cycle shows that the 55/60, 41, 31, and 25 kD protein are strongly detected during the menstrual cycle but detection is markedly reduced in endometrial samples obtained on the post-ovulatory day 4, 5, 8 and 9 or implantation window (FIG. 5). Decreased detection of the smaller sized bands was more pronounced than that observed for the larger protein band (55-60 kD). By detecting the levels of these protein bands throughout the menstrual cycle the implantation window can be determined. This provides for optimal scheduling of artificial insemination, in vitro fertilization implantation, or for optimal timing of conception.

Figure 6:
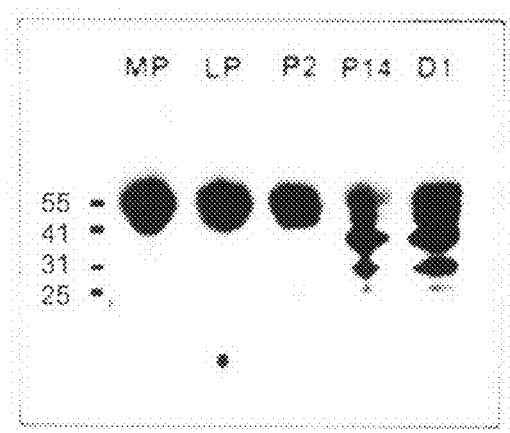
FIG. 6 is a photograph showing the immunoreactive ebaf bands in the endometrial fluid during the secretory phase; in each lane, 10 µg of extracted endometrial proteins was resolved in a 15% gel by SDS-PAGE and then subjected to Western blot analysis; the blot was probed with affinity purified rabbit antiserum to ebaf; the antiserum reacts with the protein bands in the size of 55/60, 41, 31 and 25 kD; the immunoreactivity of the bands, particularly the 41, 31 and 25 kD protein bands is markedly increased in the endometrial fluids of the late secretory and menstrual endometria; MP: mid-proliferative, LP: late proliferative, P: post-ovulatory day, D1: first day of menstruation; the size of the proteins are shown in kilodaltons.
Figure 7:
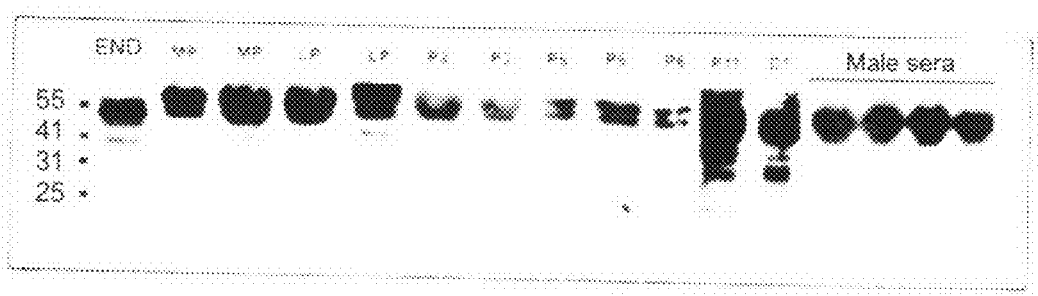
FIG. 7 is a photograph showing immunoreactive ebaf bands in human sera; in each lane, 10 µg protein was resolved in a 15% gel by SDA-PAGE and then subjected to Western blot analysis; the blot was probed with the affinity purified rabbit antiserum to ebaf; the antiserum reacts with the protein bands in the size of 55/60, 41, 31 and 25 kD; the immunoreactivity of the bands is markedly reduced in sera obtained on the post-ovulatory days 2, 3 and 6; the relative amount of the immunoreactive proteins, particularly the 41, 31 and 25 kD protein bands is markedly increased in the serum during the late secretory and menstrual phases; only the 55-60 and 25 kD proteins are abundant in male sera; the 41 kD protein band is not prominent in these sera; END: endometrial proteins from a day 1 menstrual endometrium sample were included for comparison; MP: mid-proliferative, LP: late proliferative, P: post-ovulatory day, D1: first day of menstruation; the size of the proteins are shown in kilodaltons.

The immunoreactive ebaf bands (55/60, 41, 31 and 25 kD) were detected both in the endometrial fluid (FIG. 6) as well as in sera (FIG. 7). The ebaf bands 41, 31 and 25 kD were markedly increased during the late secretory/menstrual phase both in the endometrial fluid (FIG. 6) as well as in the serum (FIG. 7). The amount of these proteins was particularly low in the serum during the early and mid-secretory phases (FIG. 7). Furthermore, these bands were similarly markedly reduced in normal fertile women during days 5-9 post LH surge and were elevated in days 10-14 post LH surge.

Figure 8:
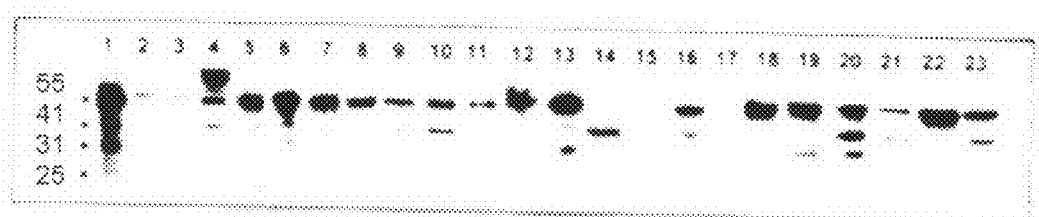
FIG. 8 is a photograph showing immunoreactive ebaf bands in endometria samples of infertile women; in each lane, 10 µg of extracted endometrial proteins isolated from the patients listed in Table 3 were resolved in a 15% gel by SDS-PAGE and then subjected to Western blot analysis; the blots were probed with the affinity purified rabbit antiserum to ebaf; the antiserum reacts with the protein bands in the size of 55/60, 41, 31 and 25 kD; different species of the ebaf protein are relatively more abundant in different patients; Lane 1: endometrial proteins from a menstrual day 1 endometrium; in this endometrium, all forms of the ebaf are abundant; Lanes 2 and 3: endometrial proteins from normal post-ovulatory day 6 endometria; in these endometria, only a smaller amount of the 55-60 kD protein species was detectable; the size of the proteins are shown in kilodaltons.

In endometrial samples of patients diagnosed as infertile the immunoreactive ebaf bands were found as abundantly as during normal menstruation and were increased over the levels found in normal fertile women during the implantation window (Table 3, FIG. 8). In different endometria, different forms of the protein were found to be the abundant species. In some, the 55-60 kD was the predominant species whereas in others, all or a single species of the ebaf was found to be prominently present (Table 3, FIG. 8).

Figure 9:
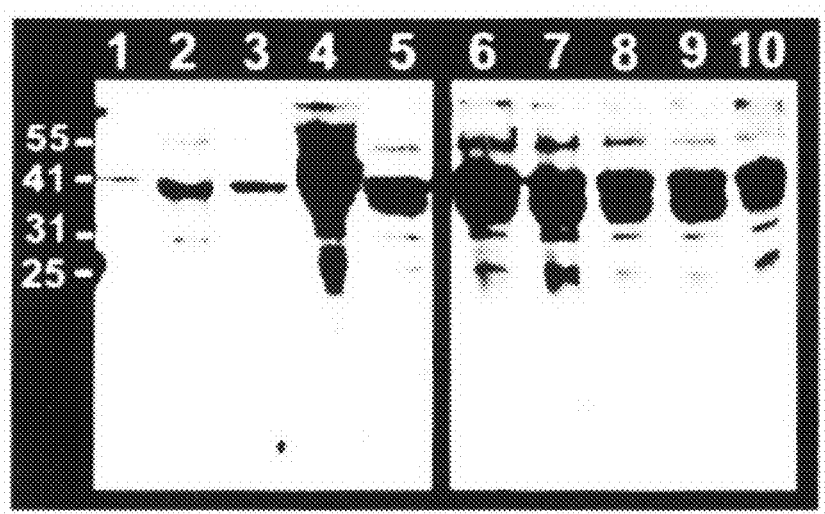
FIG. 9 is a photograph showing immunoreactive ebaf bands in endometria samples of patients diagnosed with endometriosis; in each lane, 10 µg of extracted endometrial proteins were resolved in a 15% gel by SDS-PAGE and then subjected to Western blot analysis; the blots were probed with the affinity purified rabbit antiserum to ebaf; protein bands in the size of 55/60, 41, 31 and 25 kD were abundant in the endometria of patients with endometriosis (lanes 1-10, compare with the lanes 2-3 in FIG. 8); the bands are less abundant in the endometria of endometriosis patients who are fertile (lanes 1-5) than those who are infertile (lanes 6-10); Lane 1: post-ovulatory day 8, Lane 2: post-ovulatory day 10, Lane 3: post-ovulatory day 13, Lane 4: post-ovulatory day 9, Lane 5: post-ovulatory day 9, Lane 6: post-ovulatory day 7, Lane 7: post-ovulatory day 9, Lane 8: post-ovulatory day 7, Lane 10: post-ovulatory day 8; in these endometria samples, smaller amount of the 55-60 kD protein species were detectable; the size of the proteins are shown in kilodaltons.
Figure 10:
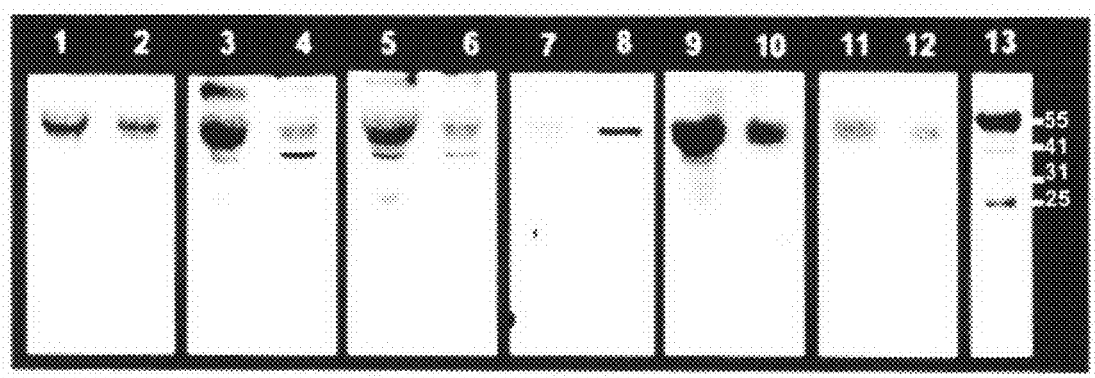
FIG. 10 is a photograph showing the immunoreactive ebaf bands in endometria samples of patients diagnosed with endometriosis with and without treatment; in each lane, 10 µg of extracted endometrial proteins were resolved in a 15% gel by SDS-PAGE and then subjected to Western blot analysis; the blots were probed with the affinity purified rabbit antiserum to ebaf; protein bands in the size of 55/60, 41, 31 and 25 kD were abundant in the endometria of patients with endometriosis (lanes 1, 3, 5, 7, 9, 11 and 12); the ebaf protein bands are less abundant in the endometria of endometriosis patients after treatment and who became pregnant after such treatment (lanes 2, 4, 6 and 8); in patients with endometriosis who remained infertile after treatment, the ebaf protein bands were not affected by the treatment (lanes 10 and 12); Lane 13: endometrial proteins from a menstrual day 1 endometrium included as control; treatment consisted of elimination of the endometriotic foci by laser (lanes 2, 6 and 10) or a single intramuscular administration of Lupron; the size of the proteins are shown in kilodaltons.

By investigating endometrial samples of fertile vs infertile patients with endometriosis, the applicant has discovered that dysregulated expression of the ebaf protein species were more pronounced in infertile women with endometriosis as compared with women with endometriosis who became pregnant (FIG. 9). By assaying for ebaf proteins, a patient with endometriosis can be advised as to their ability to conceive. Indeed, women treated for endometriosis and in which there was a decrease in ebaf proteins subsequently became pregnant. However those treated that showed an increase in ebaf proteins did not successfully conceive (FIG. 10).

Figure 11:
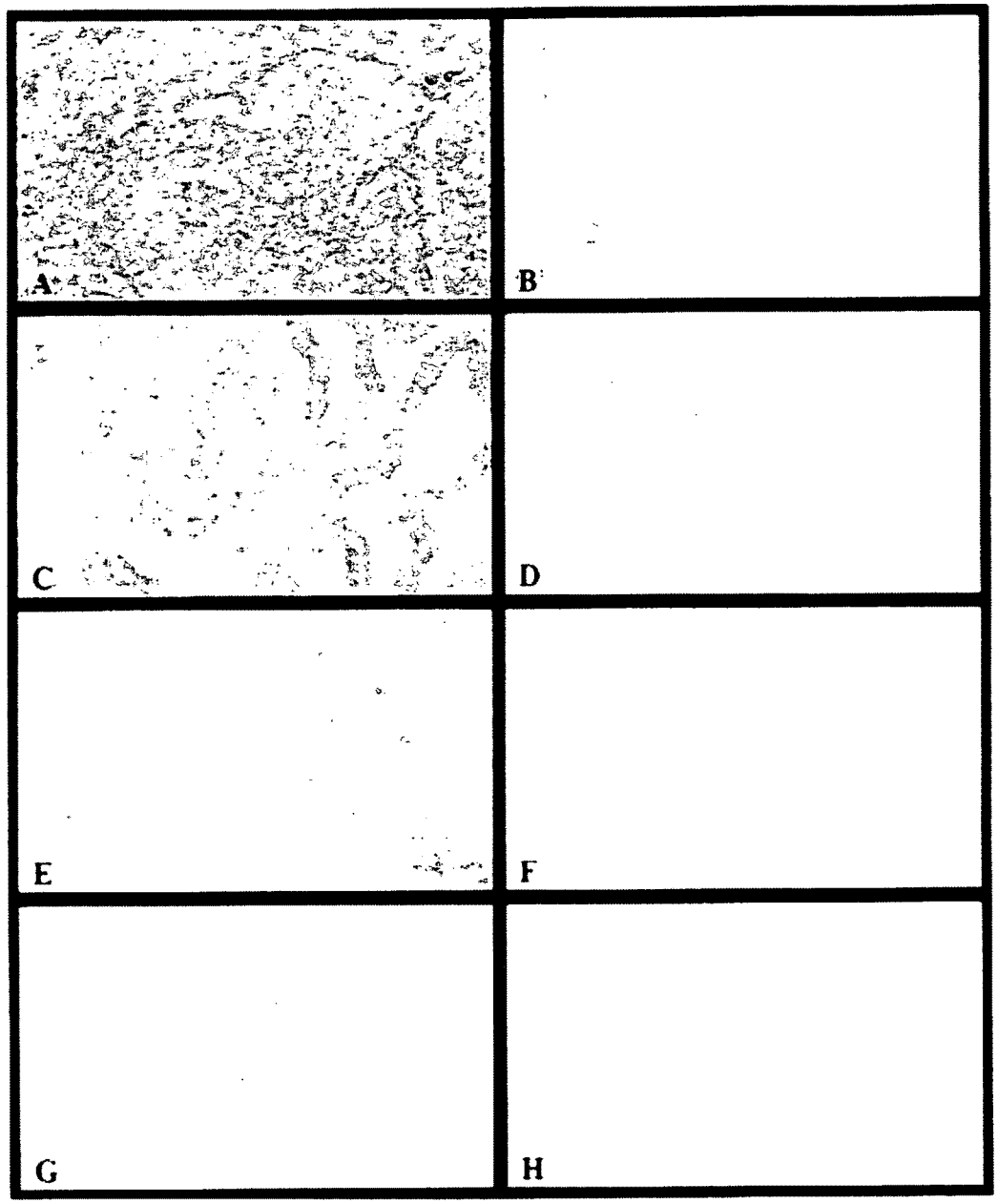
FIG. 11 is a photograph showing the endometrial glands and stroma which strongly exhibited a positive immunoreactivity (A, Table 4); in some endometria, primarily a stromal or a glandular pattern of immunostaining emerged (C, E, Table 4); in some endometria, the immunoreactivity was not easily detectable (G); the sections that were immunostained in the absence of the primary antibody did not show any evidence of immunoreactivity (B, D, F, h)
Figure 12:
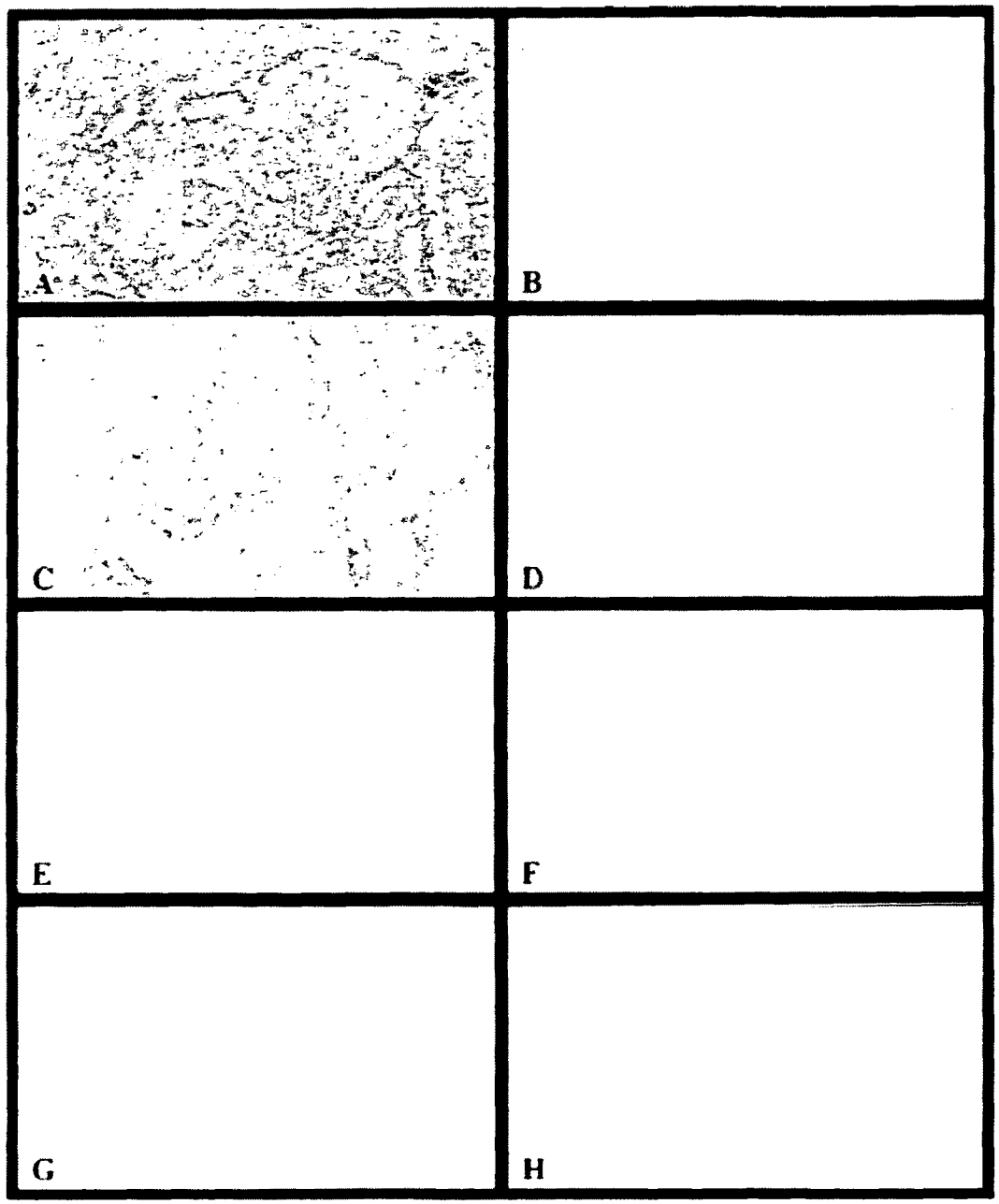
FIG. 12 is a photograph showing immunohistochemical staining of ebaf in endometrial samples of infertile women; sections of endometrial samples of infertile women were immunostained for ebaf as described in the text (A, C, E, J, I); in B, D, F, H and J, the primary affinity purified rabbit antiserum to ebaf was omitted (negative control); the diagnosis of the cases were as follows: A-B: Infertility; endometriosis, cycle day 22, C-D, unexplained infertility; luteal phase defect, E-F: Infertility; luteal phase defect, Lanes G-H: infertility; endometriosis, I-J: Infertility; luteal phase defect (Magnifications ×240)

As is known in the art, given a target protein (ebaf) and immunosera, immunohistochemical analysis can be done of endometrial tissue specimens to aid in diagnosis of infertility endometriosis and other pathologies associated with abnormal bleeding (FIG. 11). Similarly an rtPCR assay to detect ebaf mRNA can be used (FIG. 1). By using rtPCR and analysing the product for size, specific clones can be identified. In one example clones containing deletions were detected which potentially have prognostic and diagnostic value.

The ebaf is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

In the method of the present invention, the ebaf can be administered in various ways. It should be noted that the ebaf can be administered alone or in combination with pharmaceutically acceptable carriers. The compounds can be administered orally or parenterally. Implants of the compounds are also useful.

By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value as shown in the gene associated with human infertility herein above. Alternatively, the genetic material of interest encodes a suicide gene. Standard gene therapy techniques known in the art and not specifically described are generally followed as in "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Additionally, standard methods in immunology known in the art and not specifically described are generally followed as in Stites et al. (eds), *Basic and Clinical Immunology* (8$^{th}$ Edition), Appleton & Lange, Norwalk, Conn. (1994) and Mishell and Shiigi (eds), *Selected Methods in Cellular Immunology*, W.H. Freeman and Co., New York (1980). Cloning techniques are provided by the present invention as are commonly known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989)).

Immunoassays are also provided by the present invention. In general, ELISAs are the preferred immunoassays employed to assess a specimen. Both polyclonal and monoclonal antibodies can be used in the assays. The specific assay to be used can be determined by one skilled in the art.

Antibody production is provided by the present invention. Antibodies may be prepared against the immunogen, or any portion thereof, for example a synthetic peptide based on the sequence. As stated above, antibodies are used in assays and are therefore used in determining if the appropriate protein has been identified. Antibodies can also be used for removing enzymes from red cell suspensions after enzymatic conversion. Immunogens can be used to produce antibodies by standard antibody production technology well known to those skilled in the art as described generally in Harlow and Lane, Antibodies: A Laboratory Manual, Cold Springs Harbor Laboratory, Cold Spring Harbor, N.Y., 1988 and Borrebaeck, *Antibody Engineering—A Practical Guide*, W.H. Freeman and Co., 1992.

More specifically, the present invention relates to a method for use in diagnosing endometrial irregularities that is accomplished by screening an endometrial sample for the presence of ebaf. The endometrial irregularities includes infertility, endometrial bleeding or other irregularities. For the screening step, any screening tool which is viable to screen for a protein or an mRNA, is applicable. Preferably, the tool which is used is Northern blot analysis or Western blot analysis, immunohistochemical staining, or ELISA. These techniques can be accomplished by methods known to one skilled in the art.

Also, the present invention relates to a method of diagnosis and prognosis of infertility, endometriosis, menometrororrahgia, or other endometrial irregularities by first determining the optimal treatment for such irregularity. The optimal treatment or treatment response is determined by first establishing the ebaf level of the patient and then treating the patient accordingly. For example, the treatment can include down-regulating or modulating the expression of ebaf in the patient.

The endometrial sample which is utilized in the screening technique may be a tissue sample or other samples such as body fluids including but not limited to endometrial fluid, serum, urine or saliva. Further, when screening for ebaf, one could be screening either for the protein formed by ebaf or ebaf mRNA. It is important to note that this method is also used as a diagnostic tool for determining the potential for the presence of endometrial irregularities, thus enabling the physician to treat the cause of the irregularities prior to a problem actually occurring in the endometrium.

The treatment which can occur based on these irregularities would be to treat the endometrial irregularities by down-regulating or modulating the expression of ebaf which is causing such irregularities, i.e. infertility. This treatment can include gene therapy or other viable methods as are commonly known to one skilled in the art.

In another embodiment of the present invention, a contraceptive device can be formulated utilizing an effective amount of ebaf, as can be determined by one skilled in the art, in a pharmaceutically acceptable carrier. As is shown by the following examples, the presence of an up-regulation of ebaf has been shown to cause infertility in women. Accordingly, by effectively increasing the amount of ebaf in the endometrium, ebaf will functionally serve as a contraceptive thus preventing pregnancy An additional embodiment of the present invention is a diagnostic kit that allows for determining the timing of conception or endometrial receptivity levels, or infertility based on a marker. This marker is ebaf. This is accomplished by utilizing a screening tool which screens a sample for the presence of ebaf such as Western, Northern or Southern blot analysis, immunoprecipitation, immunoassay, immunohistology, PCR, ELISA or other methods that will detect the mRNA or protein insoluble or bound to a membrane. Such screening tools allows the determination of the time point at which conception is feasible, based on the amount of ebaf in the endometrium tissue or other bodily fluids. Accordingly, this will limit the problems relating to infertility or miscarriage based on the conception being too close to an up-regulation of ebaf in the female endometrium.

Additional kits can be developed for use for the diagnosis, monitoring and prognosis of a patient by determining ebaf levels in a patient's sample. This can be accomplished utilizing one of the following tests: immunohistology tests, preferably including antisera; immunoassays, preferably including antisera and peptides as positive controls; a blotting test, preferably including antisera and peptides; or PCR, preferably using at least one probe for ebaf.

One additional embodiment of the present invention is the development of an antisera for ebaf. An antibody with specificity is useful in determining the presence of ebaf, or an ebaf variant, in a sample. By variant, it is meant that an variant which is functionally relevant. Further, the peptide CASD-GALVPRRLQHRP-amide (SEQ ID NO: 3), as demonstrated in the examples below, has been shown to be effective in the development of such an antisera.

The above discussion provides a factual basis for the use of ebaf as a diagnostic tool. The method used with a utility of the present invention can be shown by the following non-limiting examples and accompanying figures.

EXAMPLES

General Methods The following Methods and Examples included herewith and incorporated by reference in their entirety further show the invention.

Methods: General methods in molecular biology: Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: A Guide To Methods And Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays: In general, ELISAs are one type of immunoassay employed to assess a specimen in the method of the present invention. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989

Antibody Production Antibodies as controls and for use in the immunoassays of the present invention as for example control antibodies can be either monoclonal, polyclonal or recombinant. Conveniently, the antibodies may be prepared against the immunogen or portion thereof for example a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W.H. Freeman and Co., 1992. Antibody fragments may also be prepared from the antibodies and include Fab, F(ab')$_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W.H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

*Recombinant Protein Purification* Marshak et al, "Strategies for Protein Purification and Characterization. A laboratory course manual." CSHL Press, 1996.

Transgenic and Knockout Methods: The present invention may provide for transgenic gene and polymorphic gene animal and cellular (cell lines) models as well as for knockout models wherein the gene associated with human female infertility is either inserted and/or the corresponding animal gene "knocked out". These models can, for example, be used for the study of therapeutics for treating infertility. These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson (1991), Capecchi (1989), Davies et al. (1992), Dickinson et al. (1993), Duff and Lincoln (1995), Huxley et al. (1991), Jakobovitz et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

For gene therapy: By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value as shown in the gene associated with human infertility herein above. Alternatively, the genetic material of interest encodes a suicide gene. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ [Culver, 1998]. These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore as used herein the is expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

Delivery of gene products/therapeutics is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms, i.e. infertility, and other indicators as are selected as appropriate measures by those skilled in the art.

Example 1

Figure 14:
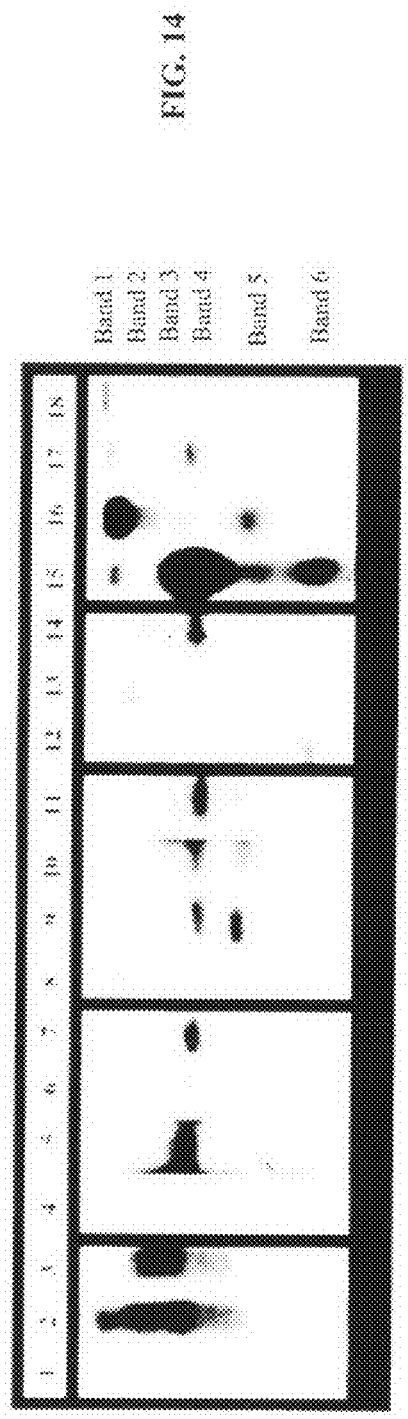
FIG. 14 is a photograph showing the results of a reverse transcription followed by polymerase chain reaction-Southern blot analysis which revealed various types of abnormal expression of the ebaf mRNA that allows various types of infertility to be differentiated from each other; lane 1 was a negative PCR control; lane 2 was a normal control; lane 3 was a menstrual bleeding control; lane 4 was a normal egg donor control; lane 5 contained a LPD abnormality; lane 6 contained a UI abnormality; lane 7 contained another UI abnormality; lane 8 contained a UI nulliparous abnormality; lane 9 contained a UI abnormality with failed IVF and GIFT; lane 10 had unexplained infertility; lane 11 had a LPD abnormality; lane 12 had a PCO clomid abnormality; lane 13 had a UI with hydrosalpinx abnormality; lane 14 had a PCO abnormality; lane 15 had an anovulatory abnormality; lane 16 had a UI abnormality with endometriosis; lane 17 had premature ovarian failure; and lane 18 had unexplained infertility.

The expression of the ebaf was examined by at least two techniques, Northern blot analysis and reverse transcription-followed by polymerase chain reaction. These are well established methodologies that are within reach of any molecular biology laboratory. Northern blot analysis has revealed the presence of an abnormally expressed 1.5 kb band in the endometria of the infertile woman which is not expressed in the endometria of the normal individual. The reverse transcription followed by polymerase chain reaction-Southern blot analysis revealed various types of abnormal expression of the ebaf mRNA that would allow various types of infertility to be differentiated from each other (FIG. 14).

Example 2

Processing of Endometria

Endometrial tissues were obtained as biopsy or curettings and from hysterectomy specimens of normal fertile women who underwent these procedures for diagnosis or treatment of non-endometrial abnormalities such as ovarian or cervical lesions. Hysterectomy specimens and each endometrial biopsy sample were rapidly processed. The data of endometrium was determined based on the morphologic evaluation of hematoxylin and eosin-stained endometrial sections using established criteria of Noyes and Hertig (1950). Each endometrial sample was aliquoted as required. However, most tissues were used as follows. About 10% of each sample was processed for paraffin sectioning and morphologic examination. About 70% was flash frozen in a dry ice/ethanol bath for isolation of RNA and the remaining 20% was frozen in OCT mounting medium (Tissue-Tek II; Miles Laboratories, Naperville, Ill.) for cryostat sectioning and in situ hybridization and immunohistochemical studies.

In Situ Hybridization

Digoxigenin-labeled sense and antisense RNAs of ebaf were synthesized by in vitro transcription of the full length cDNA cloned into pBluescript SK− using digoxigenin dUTP. After alkaline hydrolysis, the probes were subjected to agarose gel electrophoresis to determine the size of the digested RNA fragments. Dot blotting was performed on the RNA fragments to ensure that they were labeled. In situ hybridization was performed as previously described (Miller et al, 1993, Panoskaltsis-Mortari and Bucy, 1995). Briefly, frozen sections of endometria were mounted on silane-coated, RNase-free slides and fixed in 4% formalin in phosphate-buffered saline (PBS) for 15 minutes at 4° C. The tissue sections were rinsed in 2×SSC and then treated with proteinase K (1 μg/ml of 0.1 M Tris, 50 mM EDTA, 20 minutes, 37° C.) and acetylated for ten minutes at 0.1 M triethanolamine, 0.9% sodium chloride and 0.25% acetic anhydride (pH 8.0). The slides were dipped once in 2×SSC and then were dehydrated in ascending series of ethyl alcohol and air-dried. The slides were prehybridized for one hour at 37° C. in 50% formamide. 1×Denhardt's solution and 500 μg/ml tRNA, 0.3 M sodium chloride, 10 mM Tris, 1 mM EDTA (pH 8) and 10% dextran sulphate. The sections were then incubated at 55° C. overnight in the same solution containing the appropriate concentration of the probe. The amounts of labeled probes needed were empirically determined first by a series of in situ hybridization experiments using various dilutions of the probes. A sense probe was used as the control. After hybridization, slides were washed three times for ten minutes each, at room temperature in 2×SSC, and the excess SSC was removed. The sections were then incubated with RNase A (20 μg/ml) in 500 mM NaCl, 1 mM EDTA and 10 mM Tris-HCl pH 8 at 37° C. for 30 minutes to remove the non-hybridized RNA. The sections were washed three times at room temperature for 15 minutes each in 2×SSC, 1×SSC and 0.5×SSC and a final wash in 0.1×SSC at 55° C. for 45 minutes. Slides were washed in 100 mM Tris (pH 8), 150 mM NaCl for ten minutes. Sections were then blocked in 5% normal horse serum in the same buffer for 20 minutes at 37° C. Slides were incubated with alkaline phosphatase-labeled, anti-digoxigenin antibody for one hour at 37° C., washed and developed in a mixture of NBT and BCIP.

Production of the Polyclonal Antibody

Rabbit antisera were prepared in two rabbits according to established protocol against the peptide CASD-GALVPRRLQHRP-amide which resides at the carboxy end of the ebaf molecule (Reif and Allen, 1966). Keyhole limpet hemocyanin was used as the carrier protein. The coupled peptide suspended in PBS at 1 mg/ml was mixed with an equal volume of complete Freund's adjuvant. This material was mixed until it formed an emulsion and was then injected into the rabbits at six sites. A total of 300 μg of peptide was injected. Additional injections of the coupled peptide with incomplete Freund's adjuvant were performed on days 14, 28, 35 and 70 and the production bleeds were performed on days 85 and 90 after initial injection. The titers of the antisera as compared to samples of the pre-immune sera, were determined by enzyme linked immunosorbent assay. The antisera were then pooled and affinity purified using a SulfoLink Affinity column (Pierce Chemical Company, Rockford, Ill.) containing the peptide. The affinity column was made by first washing the column with PBS according to the manufacturer's instructions, followed by the addition of 1.2 mg of peptide per ml of resin. After allowing the gel and the peptide to react, the gel was washed extensively and a solution of 50 mM cysteine was incubated with the gel to react with any remaining functional groups. The column was then washed again prior to exposure to the immune serum. The column was then exposed to 20 ml of serum and 20 ml of PBS. After incubation for three hours while shaken, the serum and the gel were poured back into the Econo column and the serum flow-through was collected. The column was then washed with phosphate buffer containing 250 mM NaCl until no protein could be eluted. Then, the column was exposed to 100 mM glycine buffer (pH 2.5) and 1 ml fractions were collected into tubes containing 50 ml of 1 M Tris-HCl (pH 9.5) to neutralize the pH and to protect the integrity of the antibody. The fractions containing proteins were pooled and dialyzed in 4 liters of 5 mM phosphate buffer (pH 7.4), changing the buffer every several hours. This material was aliquoted and frozen and kept at −70° C. until used.

Western Blot Analysis

The endometrial tissue was homogenized in PEMTG buffer (50 mM potassium phosphate, 10 mM EGTA, 10 mM $Na_2MoO_4$, 12 mM thioglycerol, 10% glycerol (v/v, pH 7.0). The cystosoli endometrial proteins were prepared by collecting the 105,000 g supernatants of endometrial homogenates. The placental proteins were isolated by extracting them in 1% NP-40 in 50 mM Tris buffer pH 8.0 containing 150 mM NaCl, 0.5% Na deoxycholate, phenylmethylsulphonyl fluoride (10 μg/ml) and 0.02% sodium azide. For Western blot analysis, 75 μg of endometrial and placental proteins were loaded into each lane, separated by SDS-polyacrylamide gel electrophoresis (10% gels) and transferred to nitrocellulose membrane. Blots were incubated with TBS buffer (20 mM Tris, 500 mM NaCl, 0.05% Tween-20, pH 7.5) for 60 minutes to block unreacted sites on the nitrocellulose. Blocked sheets were incubated with the affinity purified C terminal peptide antibody to ebaf for 120 minutes and then washed in TTBS buffer and incubated with horseradish peroxide linked goat anti-rabbit IgG (BioRad, 1:3000 dilution) for 60 minutes. Immunoreactive proteins were revealed using 4-chloro-1-naphthol (01055) as the chromogen and $H_2O_2$ (0.03%) and methanol (16%) in TBS buffer (20 mM Tris, 500 mM NaCl, pH 7.5). Pre-stained molecular weight marker proteins were run on a separate lane to determine the molecular weights of the immunostained bands. As controls, primary antibody or secondary antibody was omitted from the staining reaction. The relative optical densities of the bands were measured by laser scanning densitometry as described (Tabibzadeh et al, 1989). For each band, the relative optical density was determined at three different points along the band.

Immunohistochemical Staining

Immunostaining was performed according to the ABC procedure as described (Hsu et al, 1981). Briefly, the staining consisted of fixation of the sections in 10% buffered formalin, followed by a five minute wash in PBS (0.1 M, pH 7.4). The slides were then incubated with the appropriate concentrations of the antiserum, biotinylated goat anti-rabbit IgG, and avidin-peroxidase complex. Each incubation was for 30 minutes at room temperature followed by a five minute wash in PBS. The slides were developed in the Vector VIP peroxidase kit (SK-4600, Vector Laboratories, Burlingame, Calif.). The proper concentration of the antibody was determined by serial dilutions of the antiserum. Two sets of controls were used. In one set of experiments, the primary antibody was omitted. In a second set of experiments, the antibody was preincubated with various concentrations of the peptide for 30 minutes at 37° C. prior to the application of the antiserum to the slide. Sections were viewed, evaluated and photographed at the light microscopic level without a counterstain.

Results

Figure 15:
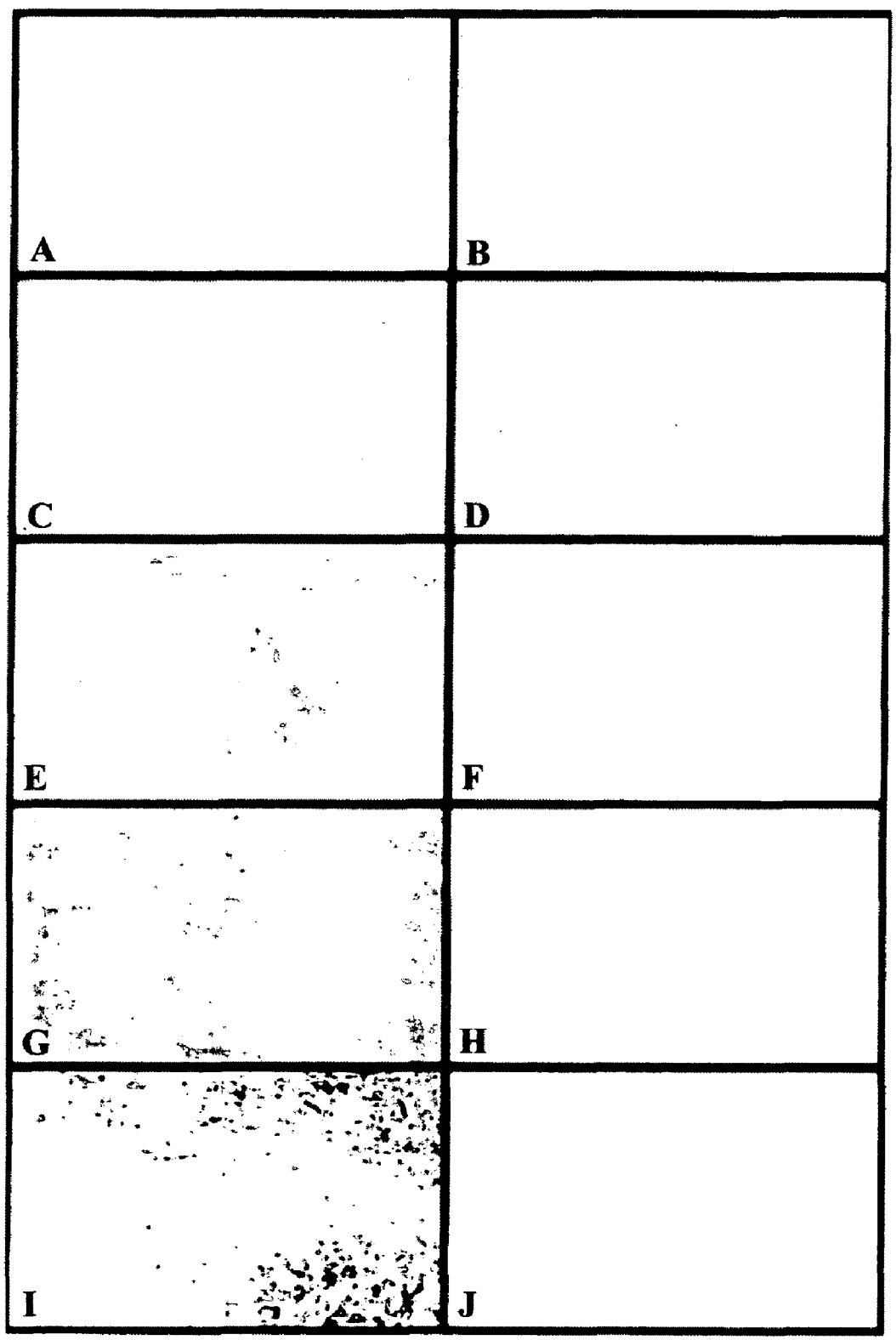
FIG. 15 is a photograph showing in situ hybridization of ebaf in normal human endometrium; sections of mid-proliferative (A) and late proliferative (C) endometria failed to show an easily detectable hybridization signal with digoxygenin-labeled, antisense ebaf RNA probe in the stroma and glands; sections of the same cases (B, D) also failed to show hybridization signal with digoxygenin-labeled, sense ebaf RNA probe; a hybridization signal was observed focally in the glandular and surface epithelium in one of the three early secretory (E) endometria with the antisense ebaf RNA probe; the sections of the same cases failed to show hybridization signal with the sense ebaf RNA probe (F); intense hybridization signal was observed in the stroma in the late secretory (G) and menstrual (I) endometria with the antisense ebaf RNA probe; hybridization signal was not detected in the sections of the same cases with the sense RNA probe (H, I); (Magnifications A-H: ×100, I-J: ×400)

Localization Of The ebaf mRNA In Human Endometrium: To localize the cells that express the ebaf mRNA in human endometrium, in situ hybridization was carried out on 18 cases. The endometria were dated to the mid-proliferative (n=3), late proliferative (n=3), early secretory (n=3), mid-secretory (n=3), late secretory (n=3), and menstrual (n=3) phases of the menstrual cycle. In the proliferative phase, a hybridization signal was not easily detectable (FIG. 15A,C). In the early and mid-secretory endometria, a hybridization signal was focally observed in some endometrial glands without a detectable signal in the stroma (FIG. 15E). On the other hand, during the late secretory and menstrual phases, an intense hybridization signal with the antisense ebaf RNA appeared in the stromal cells in the upper functionalis (FIGS. 15G,I,162A). A focal hybridization signal was still detectable in some endometrial glands (FIG. 15I, 16B). However, some endometrial glands as well as the endothelial cells of spiral arteries and the smooth muscle cells surrounding these arteries failed to show a hybridization signal (FIGS. 15G, 16A). These sense ebaf RNA failed to hybridize to any of the endometrial sections that were tested (FIGS. 16B,D,F,H,J). The characteristic menstrual cycle-dependent expression of the ebaf mRNA in human endometrium suggested that the expression of this gene may be regulated by steroid hormone(s). After menopause, the cyclic production of steroid hormones and the menstrual cycles cease. Therefore, the ebaf mRNA was attempted to be localized by in situ hybridization in three atrophic post-menopausal endometria. Hybridization signals could not be observed with antisense or sense ebaf RNA in any of these endometria (FIG. 16C,D).

Localization of the Ebaf Protein in Human Endometrium

Figure 17:
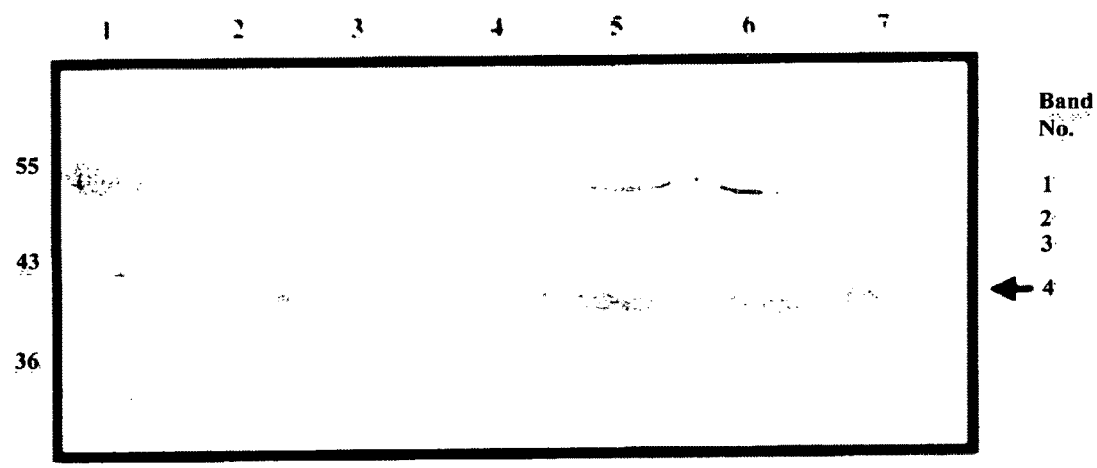
FIG. 17 is a photograph showing, in the Upper panel: Western blot analysis of the endometrial proteins; lane 1: molecular weight markers. 75 μg of placental proteins (lane 2), and cytosolic proteins of late proliferative (lanes 3-4) and the late secretory (lanes 5-7) endometria were subjected to Western blot analysis using the affinity purified rabbit antiserum against a peptide (CASDGALVPRRLQHRP-amide) SR) ID NO: 3) at the C terminal domain of the ebaf; a 41 kD protein was revealed in the placenta as well as endometria; at least three additional bands (bands 1-3) were also observed in endometria, band 3 is about 55 kD; Lower panel: the relative optical densities of the bands identified in the endometria were measured by laser scanning densitometry; the relative optical densities of the bands (1-4) is markedly increased during secretory phase; LP: late proliferative; LS: late secretory.

To localize ebaf protein in the human endometrium, polyclonal rabbit antisera were raised against the synthetic peptide, CASDGALVPRRLQHRP-amide. The antisera were pooled and purified on a peptide column. These antisera reacted with a 41 kDa protein on Western blot analysis of both placental as well as endometrial proteins (FIG. 17A). In placenta, only the 41 kDa protein was detected. However, in human endometrium additional brands were detected. These bands were larger than 41 kDa, the largest one being ~55/60 kDa (FIG. 17A). The relative optical densities of these bands were significantly greater during the late secretory phase as compared to the proliferative phase (FIG. 17B).

Figure 18:
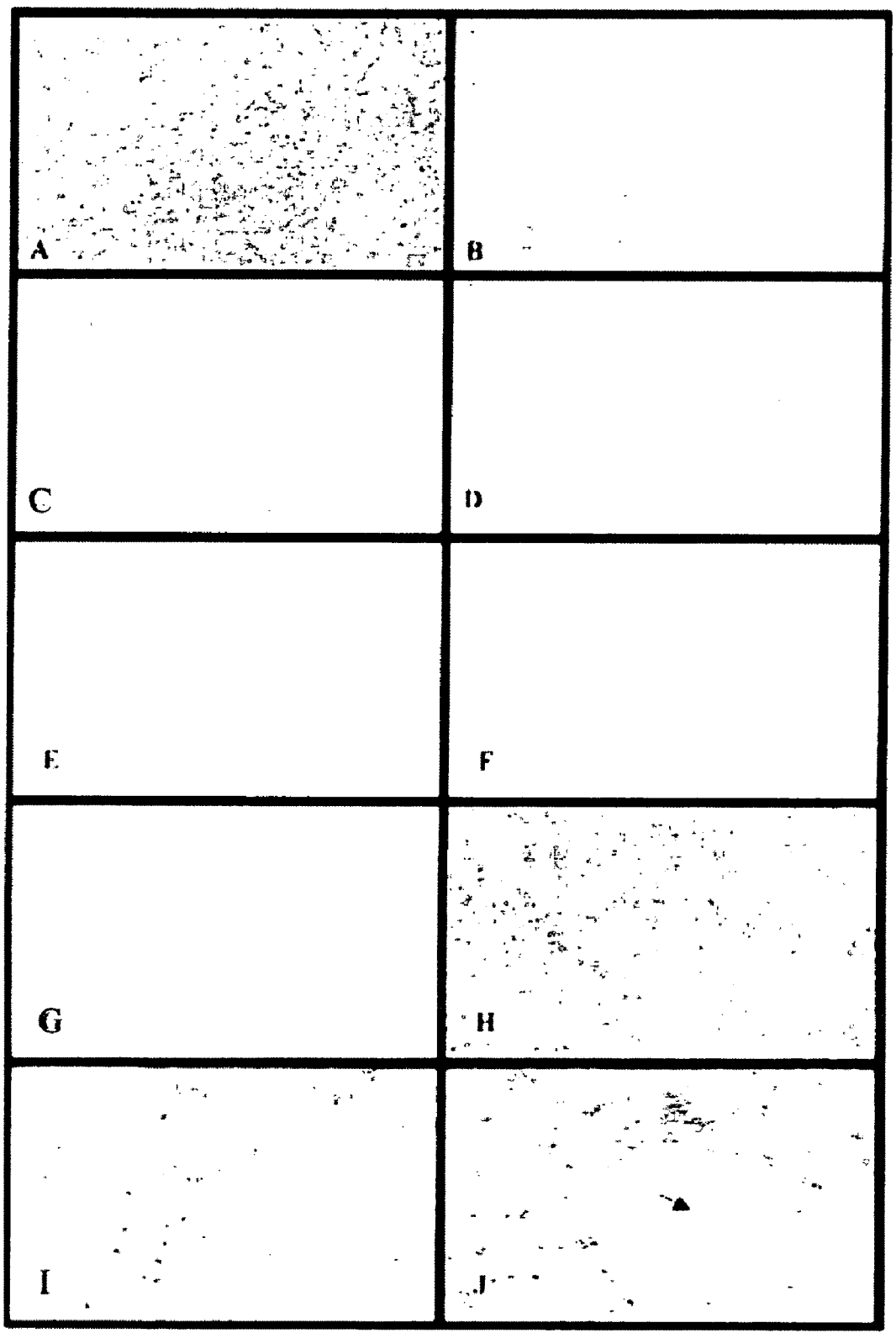
FIG. 18 is a photograph showing immunohistochemical staining of ebaf in normal human endometrium; sections of a late secretory endometrium exhibit immunoreactivity with the affinity purified polyclonal rabbit antiserum to ebaf in the stroma and glands (A); on the other hand, the sections of the same endometria fail to show any immunoreactivity with the antibody was omitted from the immunostaining reaction (B) or when the antibody is pre-incubated with the polypeptide (2 mg/ml) before applying the antibody to the section (C); the sections of a mid-proliferative (D), late proliferative (E), early secretory (POD 2, F) and mid-secretory (POD 7, G) also failed to exhibit a significant immunoreactivity with the antibody; immunostaining in the stroma and glands are easily detectable in the late secretory (H-I) and menstrual (J) endometria; arrow in J points to focal immunoreactivity in endothelial cells; (Magnifications A-H, J: ×150, I: ×240)
Figure 19A:
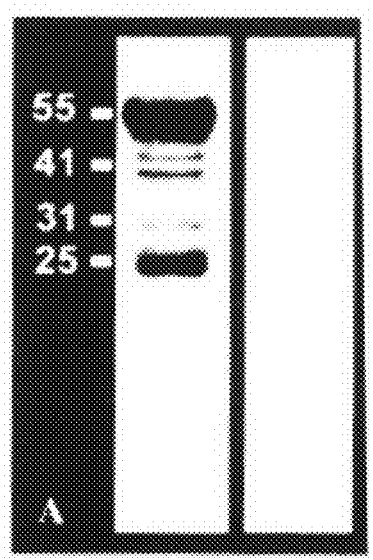
FIG. 19A and FIG. 19B are photographs showing the demonstration of immunoreactivity and specificity of the rabbit anti-serum to ebaf by Western blot analysis.
Figure 19B:
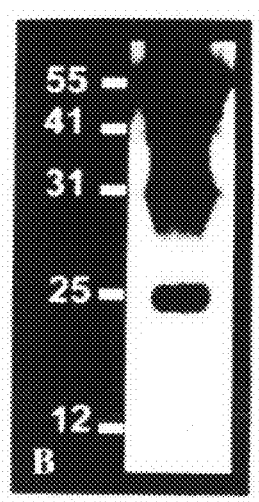
Figure 20:
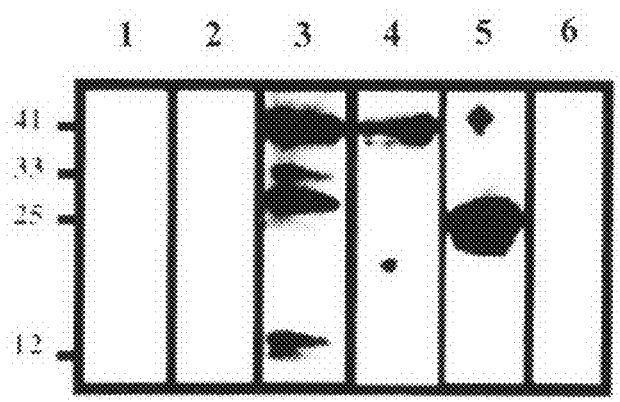
FIG. 20 is a photograph showing the Western blot analysis of the ebaf in the lysate and conditioned media of transfected cells; the conditioned media of transfected cells (lanes 1 and 3), their cell lysates (lanes 2 and 4) and recombinant *E. coli* produced ebaf (5 ng, lanes 5 and 6) were subjected to Western blot analysis and probed with affinity purified rabbit polyclonal antibody to ebaf (lanes 1-5) and a monoclonal antibody to ebaf; lanes 1 and 2: NIH-3T3 cells transfected with the anti-sense RNA prepared from the coding region of ebaf cDNA; lanes 3 and 4: NIH-3T3 cells transfected with the sense RNA prepared from the coding region of ebaf; Lane 5 and 6: recombinant *E. coli* produced ebaf; Size is shown in kD.
Figure 21:
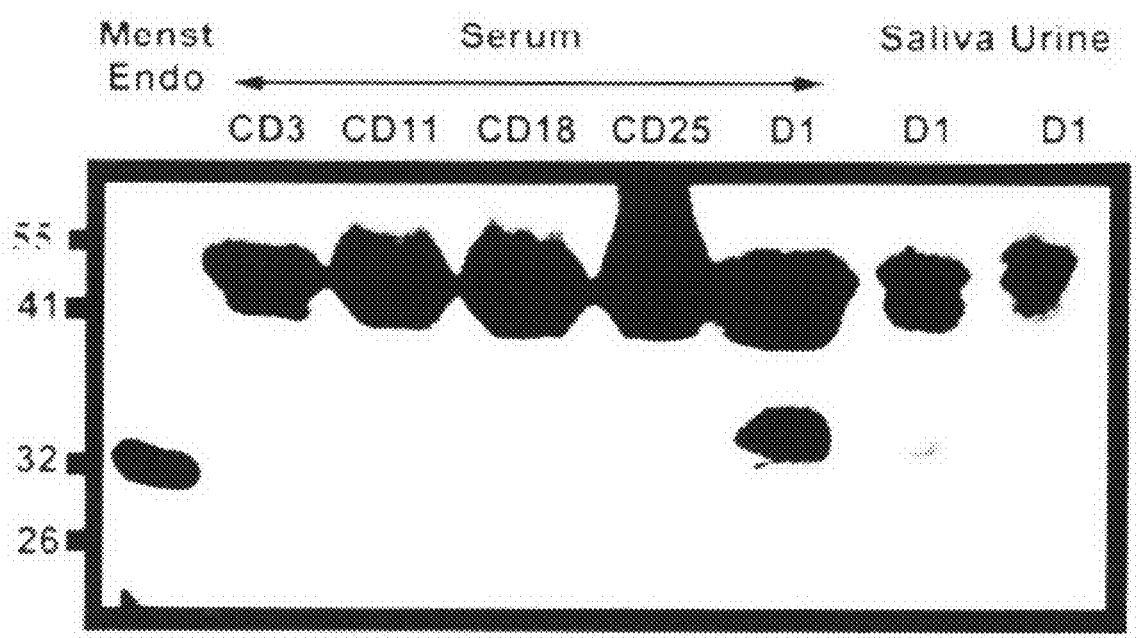
FIG. 21 is a photograph showing the demonstration of the ebaf in the serum, saliva and urine; serum samples were obtained from a normal fertile woman throughout the menstrual cycle days 3, 11, 18 and 25 and the first day of menstrual bleeding (D1); on the first day of menstrual bleeding, the saliva as was as urine was also obtained, the extracted proteins were subjected to protein gel electrophoresis; the proteins on the gel were transferred to a Nitrocellulose membrane and stained with the antibody to ebaf; the 31 kD of the ebaf protein is found on the first day of menstruation in the blood, saliva and urine.

Immunohistochemical stainings, using the same affinity purified antiserum used in the Western blot analysis, were first performed on frozen sections of a late secretory endometrium known to express ebaf mRNA by both Northern blot analysis and by in situ hybridization. When using the primary antibody, immunoreactivity was observed in the stroma and to a lesser extent in the endometrial glands of the upper functionalis (FIG. 18A). To show that such immunoreactivity is specific, the primary antibody was omitted. In the absence of the primary antibody, no specific immunoreactivity could be observed (FIG. 18B). The primary antibody was then preincubated with progressively higher amounts of the synthetic peptide, pre-incubation of the primary antibody with 1-4 µg/ml of the synthetic peptide completely abolished the immunoreactivity (FIG. 18C). Following these experiments, frozen sections of endometria dated to various phases of the menstrual cycle were subjected to immunostaining. These cases included mid-proliferative (n=3), late proliferative (n=3), early secretory (n=3), mid-secretory (n=3), and late secretory (n=3) endometria. consistent with the in situ hybridization findings, little immunoreactivity was detected in cases of proliferative endometria (FIGS. 18D,E). Similarly, there was no significant immunoreactivity for ebaf in the early secretory (FIG. 18F) or mid-secretory (FIG. 18G) endometria. In the late secretory endometria, however, staining within the glandular epithelium and surrounding stroma was observed (FIG. 18H,I). This staining pattern persisted in the menstrual endometria (FIG. 18J). Within the late secretory phase, the expression of the immunoreactive ebaf was more intense close to the surface epithelium than in the basalis. The staining decorated the cytoplasm of the epithelial and the stromal cells but no immunoreactivity was observed in the nuclei. In the late secretory and menstrual endometria, the endothelial cells did not stain for the ebaf. However, occasionally focal luminal immunoreactivity was observed in the endothelial cells (FIG. 19J).

DISCUSSION

In this report, both the mRNA and protein of the ebaf in human endometrium were localized throughout the menstrual cycle. Consistent with the data of the Northern blot analysis, in situ hybridization revealed that ebaf mRNA is expressed in the secretory phase (Kothapalli et al, 1997). During the proliferative phase, ebaf mRNA could not be detected by in situ hybridization. The first evidence for the expression of ebaf mRNA appeared during the early to mid-secretory phase. In these phases, the expression of ebaf mRNA first appeared in some endometrial glands but the adjacent stroma did not show a hybridization signal. Such mRNA expression was focal and may be below the limit of detection by Northern blotting. Consistent with the Northern blot analysis, the most intense ebaf mRNA expression appeared in the late secretory endometria and predominated in the stroma. By Northern blot analysis of the late secretory and menstrual endometria, the major mRNA species is 2.5 kb (Kothapalli et al, 1997). Therefore, it is likely that this mRNA resides primarily within the endometrial stroma.

The polyclonal rabbit antibody raised against a synthetic peptide at the C terminal domain of the ebaf reacted with a major 41 kDa protein in the placenta as well as the endometrium. In the case of lefty, which is the mouse homologue of the human ebaf, the expression of the protein in 293T cells led to formation of a non-secretory, 42 kDa protein which is the size of the pre-pro-protein (Meno et al, 1996). The predicted size of the pre-pro-protein of the ebaf is 41 kDa. The members of the TGF-β super family are synthesized as pre-pro-proteins which are cleaved at RXXR (SEQ ID NO: 2) sites to release the mature form of the protein. The predicted protein of ebaf exhibits two such RXXR (SEQ ID NO: 2) sites which are located at amino acid residues of 73-76 and 131-134 respectively (Kothapalli et al, 1997). If one of these sequences is the cleavage site, a mature protein of 294 and 236 amino acids should be produced. The deduced amino acid sequence of lefty also contained two potential cleavage sites at amino acid residues of 74-77 and 132-135, yielding mature proteins of 291 and 233 amino acids (Meno et al, 1996). Therefore, the processing of the protein and cleavage in the first versus the second RXXR site are dependent on the cell type that expresses the protein. Expression of lefty in BALB/3T3 cells led to the release of processed 25 and 32 kDa proteins into the conditioned media of the cell cultures which corresponded to cleavage at the first and second RXXR (SEQ ID NO: 2) sites respectively (Kothapalli et al, 1997). Such products were not observed in the Western blot analysis of cytosolic endometrial proteins. The inability to detect secreted proteins is attributed to the rapid release of the secreted proteins from endometrial cells. TGF-β are secreted proteins and ebaf has a signal peptide suggesting that the processed protein is also be secreted (Kothapalli et al, 1997). Western blot analysis revealed the presence of additional bands which were larger than the 41 kDa. Such products are produced as a result of post-translational modifications. It has been shown that the ebaf protein contains at least one potential glycosylation site (Kothapalli et al, 1997). The presence of this potential glycosylation site in the ebaf suggests that the protein is susceptible to modifications after translation (Kothapalli et al, 1997). Northern blot analysis or in situ hybridization did not reveal the presence of detectable ebaf mRNA in the proliferative endometria. This does not rule out, however, a low level of gene transcription and translation. This may account for the low level of ebaf protein detected by the Western blot analysis. On the other hand, the protein once produced may have a long half-life, making it detectable by the Western blot analysis. Nevertheless, consistent with the data from Northern blot analysis and in situ hybridization, both the Western blot analysis and immunohistochemical localization of the ebaf showed the presence of significantly more ebaf protein in the late secretory as compared to the proliferative phase.

Immunostaining localized the immunoreactive ebaf to both the endometrial stroma and glands. Since in situ hybridization also showed that ebaf mRNA was present in both compartments, it is likely the ebaf proteins are being synthesized in both the endometrial stroma and the glandular epithelium. However, in contrast to the focal mRNA expression seen in the epithelium, immunoreactive ebaf was more widespread in the glands, suggesting that some of the immunoreactivity may represent the receptor-bound ligand that has been internalized or passively acquired. Similarly, focal immunoreactivity in the endothelial cells may have the same origin.

A common theme has emerged from the Northern blot analysis, in situ hybridization which is established by the Western blot analysis and immunohistochemical localization of the ebaf in the human endometrium throughout the menstrual cycle. The findings show that ebaf, both at mRNA and protein levels, is prominently expressed during the late secretory phase. Such clear menstrual cycle dependent expression shows that the expression of the ebaf is decreased by steroid hormones. Consistent with this is a lack of hybridization signal for ebaf mRNA in atrophic endometria which results from cessation of cyclic steroid hormone production. Steroid hormone withdrawal leads to endometrial bleeding and tissue shedding (Tabibzadch, 1995, 1996). It has been shown that the expression of ebaf mRNA is markedly increased during endometrial bleeding irrespective of the phase of the menstrual cycle. (Kothapalli et al, 1997). Therefore, ebaf belongs to the premenstrual molecular repertoire that participates in endometrial bleeding. Conceptually, the expression of the ebaf mRNA can be used as a marker for the closing of the implantation window. Accordingly, premature expression of the ebaf during the implantation window is associated with infertility. Such premature expression of ebaf is commonly observed in infertile women, potentially allowing expression of ebaf to be used as a marker of infertility.

Example 3

Processing of Endometria and Sera

A set of endometrial tissues were obtained as biopsy or curettings and from hysterectomy specimens of normal fertile women who underwent these procedures for diagnosis or treatment of non-endometrial abnormalities such as ovarian or cervical lesions (Tables 1-2). Tissues were prepared as described above. The first set of serum samples was obtained from normal fertile subjects from whom endometrial samples were obtained and processed for paraffin sectioning and morphologic examination for tissue dating. The second set of serum samples was obtained from normal fertile subjects after LH surge.

Isolation of RNA and Northern Blotting:

The RNA was extracted by using acid guanidinium thiocyanate-phenol-chloroform extraction method as described. Briefly, the tissues were homogenized in RNA STAT-60™ in a glass or Teflon Dounce homogenizer. Each homogenate was stored for five minutes at room temperature to permit the complete dissociation of nucleoprotein complexes. Then, 0.2 ml of chloroform was added for each ml of RNA STAT-60 used. Each sample was covered and shaken vigorously for 15 seconds and allowed to stand at room temperature for two-three minutes. Following centrifugation at 12,000×g for 15 minutes at 4° C., each homogenate was separated into a lower phenol/chloroform phase and an upper aqueous phase. RNA in the upper aqueous phase was transferred to fresh tubes and mixed with isopropanol to precipitate the total RNA. After centrifugation and drying, the precipitated RNA was dissolved in diethylpyrocarbonate (DEPC)-treated water by vigorous pipetting and by a gentle heating at 55-60° C. The amount of RNA in each sample was determined spectrophotometrically and its quality was evaluated by the integrity of ribosomal RNA by electrophoresis of 20 μg of total RNA in 1% formaldehyde-agarose gel in the presence of ethidium bromide. Northern blotting was done as described. Briefly, 20 μg of total RNA of each sample was denatured at 65° C. in a RNA loading buffer, electrophoresed in 1% agarose containing 2.2 M formaldehyde gel, and blotted onto a Hybond nylon membrane using a positive pressure transfer apparatus (Posiblot, Stratagene, La Jolla, Calif.). The RNA was fixed to the membrane by UV cross-linking. Using the Prime-a-Gene kit, cDNA was labeled with [$-^{32}$P} to a high specific activity, and purified by Nick columns. Membranes were prehybridized in 50% formamide, 10×Denhardt's solution, 4% saline sodium citrate (SSC), 0.05 M sodium pyrophosphate and 0.1 mg/ml of denatured Hering sperm DNA at 42° C. for two-four hours and hybridized for 16 hours at 42° C. with $10^6$ cpm/ml of heat-denatured probe in the same buffer containing 10% dextran sulphate. Then, membranes were sequentially washed three times in 4×SSC, one time in 0.5×SSC and then one time in 0.1×SSC. All washes contained 0.1 sodium dodecyl sulphate (SDS), and were done at 65° C. for 20 minutes each. The membranes were subjected to autoradiography at −70° C. with intensifying screens. The same blot was stripped and reprobed for GAPDH. To reprobe a blot, the probe was stripped from the membrane in 75% formamide, 0.1× saline sodium phosphate ETDA (SSPE), and 0.2% SDS at 50° C. for one hours.

Production of polyclonal antibody was described above.

Western Blot Analysis:

Proteins were isolated from human endometrium or serum using TRIZOL reagent according to the manufacturer's recommendations. Briefly, after RNA and DNA were extracted from the sample, the proteins were precipitated with isopropanol and washed with 0.3 M guanidine-hydrochloride in 95% (vol/vol) ethanol. Vacuum dried protein pellets were solubilized in 10 M urea containing 50 mM dithiothreitol for 1 hour, boiled, dissolved and diluted with 4-fold concentrated Laemmli sample buffer and boiled again for 5 minutes before loading onto the gels. The protein concentration was determined by the Coomassie Plus Protein Assay Reagent. Fifteen micrograms of total protein was electrophoresed on 15% polyacrylamide-SDA gels according to the method of Laemmli, transferred to nitrocellulose membrane, and blocked for 2 hours at 25° C. with 5% non-fat milk powder in TBS buffer (150 mM NaCl and 10 mM Tris pH 7.4). Membranes were washed in TBS containing 5% non-fat dried milk powder and 0.1% (vol/vol) Tween-20 and were incubated overnight at 4° C. with rabbit polyclonal affinity-purified antiserum against ebaf (1:250 dilution of a 0.8 mg protein/ml) in TBS containing 1% (wt/vol) BSA. Membranes were washed and then incubated with biotin-labeled goat anti-rabbit antiserum (1:2000 dilution) for 90 minutes at 25° C. with ABC reagent (1:300 dilution) and developed using the enhanced chemiluminescence system.

Immunoprecipitation Of Proteins For Western Blot Analysis: Two hundred and fifty micrograms of TRIZOL-extracted protein was pre-incubated with 1 µg normal rabbit IgG and 20 µg Protein G Plus Agarose for 30 minutes at 4° C. The sample was centrifuged at 500×g for five minutes at 4° C., the pellet was discarded and then 2.5 µg of affinity-purified anti-ebaf antiserum was added to the supernatant. This preparation was incubated for two hours at 4° C. Twenty microliters of Protein G Plus Agarose was then added and the incubation was continued for an additional hour.

The mixture was centrifuged at 500×g. The pellet was washed four times with cold PBS and an equal volume of 2-fold concentrated Laemmli sample buffer was added to the pellet. The pellet was boiled for 5 minutes, centrifuged at 500×g and the supernatant was loaded directly onto a 15% polyacrylamide-SDS gel.

Immunohistochemical staining was done as described above. The proper concentration of the antibody was determined by serial dilutions of the antiserum. Two sets of controls were used, omitting the primary antibody, pre-incubated with various concentrations of the peptide for 30 minutes at 37° C. prior to the application of the antiserum to the slide. Sections were viewed, evaluated and photographed at the light microscopic level without a counterstain. The immunoreactivity was scored as negative: 0, weak: +, moderate: ++, and strong: +++.

RESULTS

The Expression Of The ebaf mRNA In The Endometria Of Patients With Infertility: As reported previously, Northern blot analysis revealed a detectable level of ebaf mRNA expression only in the late secretory/menstrual endometria. In the menstrual endometria (n=4), up to three mRNA species in the size of 2.5, 2.1 and 1.5 kb that hybridized with the full length, placentally derived, ebaf cDNA were detected (FIG. 1). As reported previously, in two normal women undergoing tubal ligation, the menstrual endometrium exhibited a significant level of the ebaf mRNA (FIG. 2, lanes 25 and 26). Consistent with previous findings, endometrium obtained during "implantation window" from a normal fertile woman who donated her egg (egg donor), exhibited a low level of ebaf mRNA expression (FIG. 2, lane 21). HL60 cell line used as a negative control did not express ebaf mRNA (FIG. 2, lane 15). The distinct temporal pattern of the ebaf mRNA expression in human endometrium suggested that ebaf belongs to a premenstrual molecular repertoire that marks the closure of the "implantation window". Therefore, the hypothesis whether infertility is associated with dyregulated expression of the ebaf mRNA during the "implantation window" was tested. Northern blot analysis was carried out on the endometria of patients with various types of infertility during the "implantation window" (Table 3). In more than 50% of infertile patients, the ebaf mRNA was detectable in the endometria of women on the post-ovulatory days 6-10 (FIG. 2). The mRNA detected was primarily the 2.1 kb species. Additional smaller bands were also detected in a smaller number of patients (FIG. 2). A high incidence of dysregulated ebaf mRNA expression, however, was identified in women with "endometriosis" and with "unexplained infertility" (Table 3, FIG. 2).

Various forms of ebaf protein In The Endometrium, Endometrial Fluid and Serum During The Menstrual Cycle: The size of the ebaf precursor protein is 41 kD. ebaf protein contains three RXXR cleavage sites which conform to the minimal requirement for efficient processing by Furin, a ubiquitous prototypical mammalian kexin/subtilisin-like endoproteinase involved in the proteolytic processing of a variety of proteins including those within the ebaf super family. If all these sites are cleaved, then products of the molecular weights of 32.3, 25.7 and 12 kD proteins are expected to the secreted (Table 2). To detect such proteins in human endometrium, an antiserum was raised against the peptide CASDGALVPRRLQHRP-amide (SEQ ID NO: 3) at the COOH terminal of the ebaf protein. When purified on a peptide column, this antibody reacted in an ELISA with the peptide (ELISA reading: 23,500) and its reactivity could be inhibited by pre-incubation of the antibody with 100 fold excess of the peptide (ELISA reading: 700). The antiserum reacted with a number of endometrial proteins on the Western blot analysis which included a 41 kD protein, as well as 31, 25 (25/27) and 55 (55/60) kD protein bands (FIG. 3). These bands were not detected when the antibody was omitted during the immunostaining procedure. When adequately resolved, the 41 kD protein appeared as a doublet. The immunoreactivity of the antiserum with these bands was completely abolished by pre-incubation of the antiserum with 100 fold excess of the peptide (FIG. 3). These findings show that the antibody reacts specifically with the ebaf. However, the predicted 12 kD protein was not detected. To show that such protein exists in human endometrium, the endometrial proteins were immuno-precipitated by the antiserum. The immunoprecipitated proteins were subjected to SDS-PAGE and examined by Western blot analysis. In addition to the bands detected by Western blot analysis, an additional 12 kD protein band was detected (FIG. 4). To show the temporal pattern of synthesis and/or secretion of endometrial ebaf protein throughout the menstrual cycle, Western blot analysis was carried out on a number of endometria obtained from various phases of the menstrual cycle (FIG. 5). The immunoreactive ebaf bands (55/60, 41, 31, 25 kD) were detected during the menstrual cycle (FIG. 5). However, this immunoreactivity was greatly reduced during the "implantation window" (FIG. 5). The disappearance of the smaller in size bands was more pronounced than that observed for the larger protein band (55/60 kD), apparently due to excessive amount of this latter protein. ebaf has a signal peptide and appears to be a secreted cytokine. Therefore, the endometrial fluid and the sera of normal fertile subjects for the presence of immunoreactive ebaf was examined. The immunoreactive ebaf bands were detected both in the endometrial fluid (FIG. 6) as well as in sera (FIG. 7). The ebaf bands 41, 31 and 25 kD were relatively more abundant during the late secretory/menstrual phase both in the endometrial fluid (FIG. 6) as well as in the serum (FIG. 7). The amount of these proteins was particularly low in the serum during the early and mid-secretory phases (FIG. 7). To further validate these findings, sera were obtained from normal fertile women on different days after the lutenizing hormone (LH) surge. The amount of the immunoreactive ebaf bands were markedly reduced during days 5-9 post LH surge and were elevated in the days 10-14 post LH surge. In the male sera, the 55 (55/60), 41 and 25 kD proteins were detected, however, the 31 kD form of the ebaf protein was not found in these sera (FIG. 7).

Expression Of The ebaf Protein In The Endometria Of Patients With Infertility: Next the expression of the ebaf proteins in the endometria of infertile patients was examined (Table 3, FIG. 8). The immunoreactive ebaf bands were found in differing amounts in the endometria of infertile women. In some infertile women, the immunoreactive ebaf bands were as abundant as those found during the menstruation and more than that found in the endometria of normal fertile women during the "implantation window" (Table 3, FIG. 8). In different endometria, different forms of the protein were found to be the abundant species. In some, the 55/60 kD was the predominant species whereas in others, all or a single species of the ebaf was found to be prominently present (Table 3, FIG. 8).

To determine whether the dysregulated immunoreactive ebaf was the correct immunoreactivity was examined in the endometria of patients with endometriosis. In some women, the endometriosis is associated with infertility whereas in others, its presence does not preclude pregnancy. As compared with the control fertile endometria, the ebaf protein bands were as abundant as those found during the late secretory and menstrual phase (FIG. 9, compare with normal control shown in FIG. 8). With the exception of one patient, however, this dysregulated expression of the ebaf protein species was more pronounced in infertile women with endometriosis as compared with women with endometriosis who became pregnant (FIG. 9). The ebaf immunoreactivity was then examined in the endometria of 6 infertile women with endometriosis who underwent treatment for their infertility (FIG. 10). Four patients, in whom treatment led to a decrease in the immunoreactive ebaf bands, subsequently became pregnant after treatment (FIG. 10). On the other hand, two additional patients in whom the treatment was associated with an increase in the immunoreactive ebaf bands, did not become pregnant (FIG. 10).

The immunoreactive ebaf protein can be detected in the stromal and endometrial epithelial cells in the late secretory endometria. The immunoreactive ebaf protein bands were not detectable in the early and mid-secretory endometria. To localize the cells that expressed the ebaf in the endometria of infertile patients, immuno-histochemical stainings were carried out on the frozen sections of endometria obtained from early to mid-secretory phases (Table 4). In some endometria, both the endometrial glands and stroma strongly exhibited a positive immunoreactivity (FIG. 11A, Table 4). In some endometria, primarily a stromal or a glandular pattern of immunostaining emerged (FIG. 11C, 11E, Table 4). Yet, in some endometria, the immunoreactivity was not easily detectable (FIG. 11G). The sections that were immunostained in the absence of the primary antibody did not show any evidence of immunoreactivity (FIG. 11B, 11D, 1F, 11H).

DISCUSSION ebaf was identified as a member of the premenstrual/menstrual molecule repertoire in human endometrium. By Northern blot analysis, the ebaf mRNA was abundant in the late secretory and menstrual endometria. Based on the amino acid component of the ebaf, the size of the precursor protein was estimated to be 41 kD. Consistent with this size, a 41 kD protein band which appeared as a doublet, when adequately resolved, was detected in the Western blot analysis of the endometrial proteins. The NIH-3T3 cells transfected with ebaf, the also expressed the 41 kD protein. Presence of a signal peptide suggested that ebaf may be a secreted protein. Three potential cleavage sites exist within the ebaf precursor leading to 32.3, 25.7 and 12 kD secreted proteins. The Western blot analysis of endometrium, endometrial fluid, and serum revealed protein bands of 31 and 25 kD. The relatively lower abundance of this protein accounts for the lack of its detection by the Western blot analysis. However, when immunoprecipitated, a ~12 kD protein was also detected in the endometrium. Similarly, the transfection of the NIH-3T3 cells with ebaf led to the secretion of a 32 and 25 kD as well as the ~12 kD protein. In addition to these bands, a 55 (55/60) kD protein band was detected by the Western blot analysis in the endometrium, endometrial fluid and serum. Since the immunoreactivity of the antibody with this band could be inhibited by pre-incubation with the peptide, it seems that this band may represent ebaf protein, which in view of its size, may be a post-translationally modified product. Some of the proteins detected in the tissue lysates of endometrium may be secretory products that reside outside the cells and which ultimately enter the peripheral circulation. Consistent with this hypothesis, the ebaf protein could be detected in the endometrial fluid and sera. The immunohistochemical staining showed that some of the protein is detectable within the endometrial cells. The presence of the 41 kD precursor protein in the serum is unusual. However, the 41 kD was also secreted from the transfected cells indicating that it may be released to the outside of the cells. It is interesting to note that serpins that inhibit Furin and which lack the typical cleavable N-terminal signal sequence have been found to reside extracellularly. ebaf protein was found in the male sera indicating that sources other than uterus exist in the body that make ebaf. Using Northern blot hybridization, it was shown that the ebaf mRNA is expressed, at a low level, in the pancreas, rectum, ovary and testis. The mRNA of many cytokines is expressed at a low copy number, yet, this is sufficient for the translation of an adequate number of cytokine molecules active in the tissue micro environment. This is the basis for the detection of the ebaf protein by Western blot analysis in the endometrium during the proliferative phase of the menstrual cycle, in presence of a low level of ebaf mRNA. The 25 kD and not the 31 kD protein bands were detected in the male sera suggesting that only the 31 kD protein may be uterine specific. Thus, the amount of this protein species in the serum reflects the amount of the ebaf synthesized by the endometrium.

The production and/or release of the ebaf protein in human endometrium and the serum was dependent on the phase of the menstrual cycle. The amount of the protein was lowest during the "implantation window". Based on these findings, it was determined that successful implantation occurs in the presence of a low level of ebaf protein in human endometrium and that a high level would be associated with infertility. Consistent with this hypothesis, Northern blot analysis showed that the expression of the ebaf mRNA is up-regulated in the endometria of infertile patients during the "implantation window". In over 50% of endometria from infertile patients, the ebaf mRNA was up-regulated during the "endometrial receptivity period". The infertility in these women was associated with endometriosis, polycystic ovary, bilateral tube occlusion, anovulatory cycle, luteal phase defect, premature ovarian failure and habitual abortion. In some women, the underlying basis of infertility remained unknown (unexplained infertility). Therefore, the dysregulated expression of the ebaf mRNA in endometrium seems to be a common event in diverse types of infertility. An additional, smaller ebaf mRNA was also detectable in the endometria of some of infertile women. Women with endometriosis exhibited such a dysregulated expression of ebaf protein in endometrium. However, there was relatively more ebaf protein in the endometria of endometriosis patients who were infertile. The dysregulated expression of the ebaf by the endometrium could be reversed by an appropriate treatment strategy. In four patients who were treated, when such dysregulated expression was reduced, the patients subsequently became pregnant. However, both women in whom the treatment failed to adequately suppress the dysregulated expression of the ebaf by the endometrium, failed to become pregnant. It is conceivable that the dysregulated expression of the ebaf protein in the endometria of women may lead to abortion. In fact, it has been estimated that in up to 30% of normal fertile women, pregnancy is ended with abortion. Furthermore, nearly 50% of early pregnancy losses occur when implantation occurs after the post-ovulatory day 10 when the amount of the ebaf protein is relatively abundant in endometrium. Therefore, the dysregulated expression of the ebaf can be used as a marker of a receptive and/or fertile endometrium.

Example 4

Methods

Processing of endometria was as described above.
Isolation of RNA and Northern blotting was accomplished as described above.
Cloning, Sequencing And Analysis Of DNA Sequences:
Each cDNA was sequenced with Sequences ver. 2.0 (Amersham, Life Sciences, Arlington, Ill.) using the dideoxy chain termination method. The sequence was analyzed by DNAsis for windows (Hitachi Software, San Bruno, Calif.).
Reverse Transcription-Polymerase Chain Reaction: Total RNA was dissolved in RNAse-free water and incubated at 37° C. with 40 U DNAse I (Gibco-BRL Life Technologies) for 30 minutes. The reaction was terminated by the addition of EDTA (20 mM) and incubation for ten minutes at 6.5° C. Total RNA was precipitated overnight at −80° C. by the addition of three volumes of absolute ethanol-sodium chloride mixture. The quantity of the RNA was determined spectrophotometrically.
Total RNA was transcribed to cDNA as described. Briefly, total RNA was reverse transcribed in a 20 μg volume containing 2 μg RNA; 0.2 μg oligo (dT), 1.25 mM of each of dATP, dCTP, dGTP, dTTP, 5 U AMV reverse transcriptase; 10 mM MeHgOH, 88 mM β-mercaptoethanol; 10 U RNAsin; 100 mM Tris-HCl (pH 8.3); 40 mM KCl and 10 mM MgCl2. After 60 minutes of incubation at 42° C., the reaction mixture was heated to 95° C. for three minutes and then the reaction mixture was placed at 0° C.

PCR was carried out as described using the 5' primer (B2P9): TCAGCGAGGTGCCCGTACT (SEQ ID NO: 4) and 3' primer (B2P1): AGTTCTTAGAGCTGAAGCC (SEQ ID NO: 5). Briefly, 1 μg of reverse transcribed RNA was amplified with 0.5-1 μM of each of the 5' and 3' primers specific for ebaf in a 50 μl reaction volume containing 1.25 U AmpliTaq DNA polymerase, 1.25 mM $MgCl_2$, 20 μM of each of dATP, dCTP, dGTP, dTTP, 10 mM Tris-HCl (pH 8.3), 50 mM KG, and sterile distilled water. Negative control tubes received non-reverse transcribed RNA to verify absence of contaminating DNA. Positive control tubes received all the reagents in the reaction mixture, however, the primers used were specific for β-actin. The reaction mixture was overlayered with 50 μl of mineral oil and the tubes were heated for 5 minutes at 95° C. After initiation of temperature cycling, samples were amplified for 25 cycles. The denaturation temperature was 95° C. for one minute, annealing temperature was 55° C. for one minute and the extension temperature was 72° C. for 2.5 minutes. Temperature cycling was concluded with a final extension at 72° C. for ten minutes and the reaction products were maintained at 4° C. Amplified products were resolved in a 2% agarose gel and the bands were visualized by ethidium bromide staining. The 123 basepair DNA ladder was used as molecular weight markers.

Production of polyclonal antibody was as described above.
Immunohistochemical staining was carried out as described above.
Sections were viewed, evaluated and photographed at the light microscopic level without a counterstain. The immunoreactivity was scored as negative: 0, weak: +, moderate: ++ and strong: +++.

Results

Figure 13:
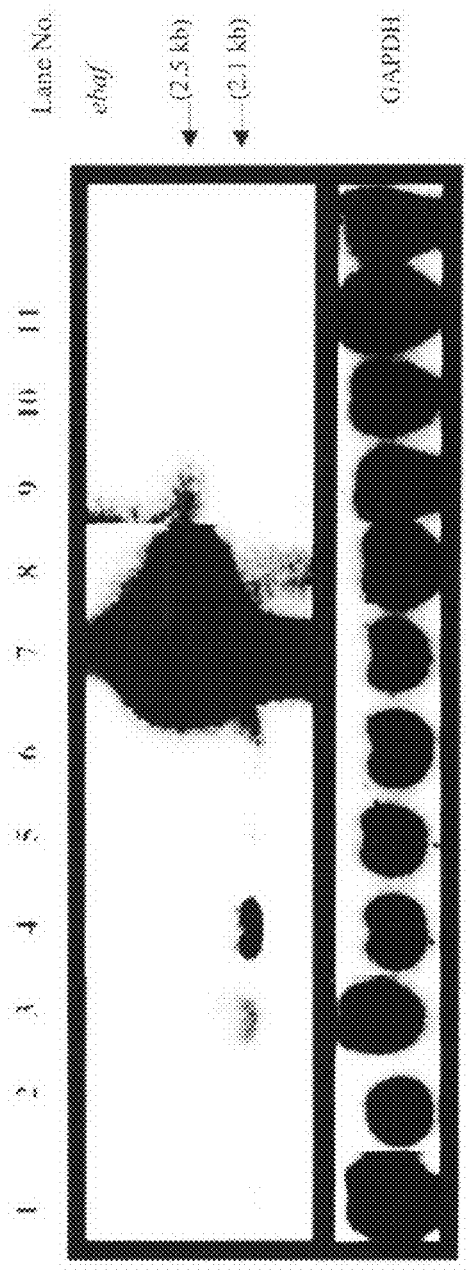
FIG. 13 is a photograph showing the expression of ebaf mRNA in the endometria of normal subjects and patients with unexplained infertility; the RNA's from endometria were subjected to Northern blot analysis and the endometria were obtained from patients with unexplained (lanes 1-6) on the post-ovulatory days 20-23; RNA from several normal endometria were included as controls (lanes 7-12), these endometria were dated to day 1 of menstruation (lanes 7-8), post-ovulatory days 13/14 (lane 9), post-ovulatory day 5 (lane 10) and mid-proliferative endometria (lanes 11-12); the same blots were hybridized with a probe to GAPDH, and strong expression of 2.5 kb ebaf mRNA is seen in the endometria of normal subjects with menstrual bleeding; the 2.1 kb mRNA of ebaf is aberrantly and prematurely expressed in the endometria of patients.

Premature Expression Of The ebaf mRNA In Endometria Of Patients With Infertility: As reported previously, Northern blot analysis did not reveal any ebaf mRNA in the proliferative, mid and late secretory endometria. During the late secretory phase, one major mRNA species in size of 2.5 kb was observed (FIG. 1). However, in the menstrual endometria (n=4), in addition to the 2.5 kb ebaf mRNA, other bands were detectable. When adequately resolved, at least three mRNA species in the size of 2.5, 2.1 and 1.5 kb that hybridized with the full size placental derived ebaf cDNA were detected (FIG. 1). To verify this finding, the mRNA of normal endometria were reverse transcribed and then PCR(RT-PCR) amplified using a primer set (B2P9, B2P1) which framed the coding region of the ebaf cDNA (FIG. 13). During the proliferative phase of the menstrual cycle, with the exception of one case, Southern blot analysis using the [$^{-32}$P]-labeled full length ebaf cDNA as the probe did not show any amplified products. In one proliferative endometrium, the size of the amplified product was nearly 1200 bp (FIG. 13). During the early, mid and late secretory phases, additional bands that were smaller in size were detected (FIG. 13). However, during menstrual phase, at least five discrete amplified bands were detected. One band was of expected size (1617 bp). However, four smaller bands were also easily detectable (FIG. 13). After RT-PCR of RNA from a menstrual endometrium, the gel residing between bands 1 and 2 as shown in FIG. 13 was removed, the DNA was eluted, and cloned. Using the same primers used in the RT-PCR, clones were PCR amplified and three clones that had inserts that were smaller in size than expected were sequenced. These clones had deletions that were respectively, 458, 196 and 98 bp in length within the coding region of the ebaf cDNA (FIG. 14).

The pre-menstrual/menstrual expression of the ebaf mRNA suggested that this gene belongs to the molecular repertoire that participates in endometrial bleeding. Conceptually, the expression of the ebaf mRNA may be used as a marker for closing of the implantation window. Therefore, premature expression of the ebaf during the implantation window may be associated with infertility. Therefore, Northern blot analysis of endometria of patients with various types of infertility was carried out. The endometria were obtained from the infertile patients during the "implantation window" when ebaf mRNA can not be detected by the Northern blot analysis in normal women (Table 5). In two women who were undergoing tubal ligation, the menstrual endometrium exhibited the 2.5 kb mRNA and in one endometrium, the 2.1 and 1.5 kb mRNA could be detected (FIG. 2). There was no mRNA in the HL60 cell line that was used as a negative control (FIG. 2). Additional smaller bands were also detected in a smaller number of the patient population that were examined (FIG. 2). As shown previously, such bands were not detectable in the endometria of normal individuals in the same phase of the menstrual cycle.

Figure 16:
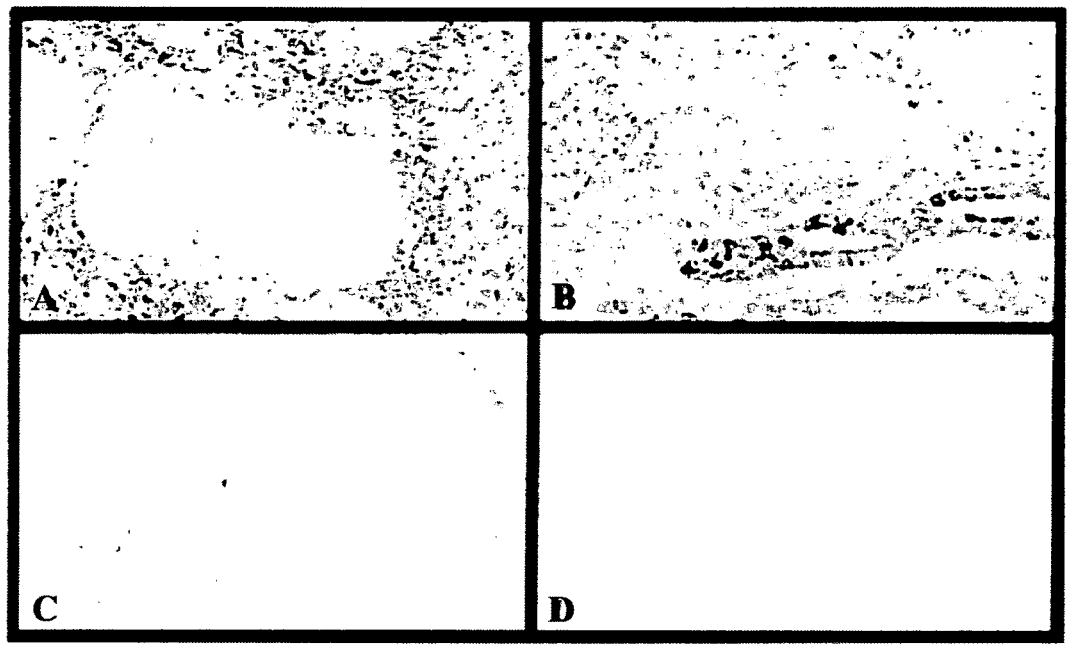
FIG. 16 is a photograph showing in situ hybridization of ebaf in normal human endometrium; (A) Sections of late-secretory endometria exhibit hybridization signal mainly in the stroma; glandular epithelia (Gland) fails to exhibit hybridization signal with the antisense ebaf RNA probe; (B) hybridization signal with the antisense ebaf RNA probe is present in the stroma (small arrow), focally in the endometrial glands (large arrow) and is absent in the endothelial cells (arrowhead) in a late secretory endometrium; (C) hybridization signal is not detected in an atrophic endometrium with the sense ebaf RNA probe; (D) hybridization signal is not detected in an atrophic endometrium with the sense ebaf RNA probe (large arrow: glands; small arrows: stromal cells); (Magnifications A-B: ×400, C-D: ×100).

To validate these findings, the RT-PCR-Southern blot analysis was performed on the cDNAs of the endometria of infertile patients using the B2P9, B2P1 as primers (Table 6). In all endometria, a 1200 bp fragment was detectable (FIG. 16). In some endometria, this was the only band that was amplified (FIG. 16). However, in other patients, a range of other abnormally expressed bands were also detected (FIG. 16). In some endometria additional smaller bands were amplified. In different individuals, up to four such amplified products were detected (FIG. 16). In some patients, the 1617 bp amplified fragment which was normally amplifiable in normal endometria during menstruation was also detected (FIG. 16).

Premature Expression Of ebaf protein. In The Endometria Of Infertile Patients: To localize the ebaf protein in endometrium, two polyclonal rabbit antisera were raised against a sequence (CASDGALVPRRLQHRP) (SEC, ID NO: 3) that resides at the carboxy terminal end of the express ebaf. The pooled polyclonal anti-sera, affinity purified over a peptide column, reacted with a 41 kD protein on the Western blot analysis of both placenta as well as endometria, which is the size of the pre-pro-protein (unpublished data). Immunohistochemical stainings were first carried out using the same antiserum on frozen sections of a late secretory endometrium known to express ebaf mRNA by both Northern blot analysis and by in situ hybridization. Immunoreactivity could be observed in the stroma and to a lesser extent in the endometrial glands of the upper functionalis (FIG. 17A). To show that such immunoreactivity is specific, the primary antibody was omitted. In the absence of the primary antibody no specific immunoreactivity could be observed (FIG. 17B). Furthermore, the primary antibody was pre-incubated with progressively higher amounts of the synthetic peptide. Pre-incubation of the primary antibody with an appropriate concentration of the synthetic peptide (1-4 µg/ml) completely abolished the immunoreactivity (FIG. 17C). Additional immunostaining using late secretory and menstrual endometria showed the same pattern of immunostaining. However, frozen sections of endometria dated to early and mid secretory phase failed to reveal any positive immunoreactivity (FIG. 17D). Then, the frozen sections of endometria obtained from early to mid-secretory phases of infertile patients were subjected to the immunostaining (Table 7). Three different patterns of immunoreactivity were detected. In some endometria, both the endometrial glands and stroma strongly exhibited a positive immunoreactivity (FIG. 18A, Table 7). In some endometria, primarily a stromal pattern of staining was visualized (FIG. 18C, Table 7). In other endometria, a glandular pattern of immunostaining emerged (FIG. 18E, 18J, Table 7). Yet, in some endometria, the immunoreactivity was not easily detectable (FIG. 18I). The sections that were immunostained in the absence of the primary antibody did not show any evidence of immunoreactivity (FIG. 18B, 18D, 18F, 18H, and 18J.

DISCUSSION ebaf was identified as a member of the premenstrual/menstrual molecular repertoire. By Northern blot analysis, the 2.5 kb mRNA of the ebaf was detectable in the late secretory and menstrual endometria. In addition, when adequately resolved, at least two additional bands of 2.1 and 1.5 kb were detectable. This finding suggests that ebaf mRNA has spice variants. To further test this hypothesis, RT-PCR of a region spanning bases 143 to 1761 of the ebaf cDNA was carried out. The expected 1617 bp fragment could be amplified from menstrual endometria. However, at least four additional bands which were smaller in size were also detected. From these, a 1200 bp fragment could also be amplified from the secretory and one proliferative endometrium. However, such products could not be detected in other proliferative endometria. These findings are consistent with the reported absence of the 458, 196 and 98 bp mRNA in the proliferative endometria. Presence of these smaller in size amplified products in human endometrium is consistent with existence of splice variants of ebaf mRNA. Sequencing of some of these products showed that their sequence matches the known sequence of the ebaf cDNA. However, deletions in the size of 458, 196 and 98 bp were detected in these amplified products.

Northern blot analysis of endometria of infertile patients during the receptive phase of the menstrual cycle showed premature expression of the 2.1 kb ebaf mRNA which was present only during menstruation in normal endometria. Over 50% (14/26) of endometria from infertile patients exhibited this mRNA species. The infertility in these women was associated with endometriosis, polycystic ovary bilateral tube occlusion, anovulatory cycle, luteal phase defect, premature ovarian failure and habitual abortion. In come women, the underlying basis of infertility remained unknown (unexplained infertility). Therefore, premature expression of the ebaf mRNA in endometrium is a common event in diverse types of infertility. An additional smaller ebaf mRNA was also detectable in endometria of some of infertile women. Consistent with the premature expression of the ebaf mRNA in these endometria, RT-PCR-Southern blot analysis revealed presence of amplified products in various sizes in endometria of infertile women during the receptive phase of the menstrual cycle. A 1200 bp amplified product was universally found in these endometria. However, in eight of 14 patients, additional products larger than 1200 bp was found. This band is nearly 400 base pair smaller than the expected product (1617 bp) and may correspond to the 2.1 mRNA in the Northern blot analysis. In five patients, the product expected only during the menstrual phase (1617 bp) was found. These findings show that various types of infertility are associated with the premature expression of ebaf mRNA in endometrium.

To validate these finding, the immunoreactive ebaf was localized by immunohistochemical staining in endometria of patients with infertility. As expected, the immunoreactive ebaf was not detectable in early-mid secretory endometria. The expression of the immunoreactive ebaf became detectable more strongly in the stroma than in the endometrial glands during the late secretory and menstrual phases. These findings validate the data from Northern blot analysis and the RT-PCR-Southern blot, that the major transcriptional activity for the ebaf takes place during premenstrual and menstrual phase of the cycle. In contrast to the lack of immunoreactive ebaf in normal endometrium during the receptive phase of the cycle, the immunoreactivity for the ebaf was detectable in nearly 50% (9/19) endometria from infertile women. Three major patterns of immunostaining emerged. The immunoreactive ebaf was present both in the glands and stroma (4/9), in the stroma (4/9) and only in glands (1/9). In the endometria of some infertile women (10/19), the immunoreactive ebaf was not detectable. The underlying basis for the glandular versus stromal immunoreactivity may be based on the expression of different forms of the ebaf mRNA in these endometrial compartments. The antibody used in this study was raised against a sequence at the C-terminal of the ebaf. Therefore, this antibody may react with various forms of ebaf and does not allow addressing differential expression of the ebaf in glands versus stroma.

Endometrium is a unique tissue which, in response to the systemic steroid hormones, is prepared after ovulation for implantation. The molecular repertoire of the implantation window is therefore likely to be exquisitely sensitive to these signals. Any imbalance in regulatory mechanisms that drive endometrium during the secretory phase may lead to lesions within such molecular repertoire. For example, during an anovulatory cycle, the production of the systemic steroid hormones is aberrant. In luteal phase defect, this aberrancy is more subtle and leads to a lag in the maturation of endometrium. The means by which the disease processes such as endometriosis, or tubal lesions may affect endometrium is not well understood. However, in women with infertility, the treatment of these processes increases the chance of conception, suggesting endometrium as the target organ for the effects of these diseases. In some instances, the underlying basis for the infertility remains unclear (unexplained infertility). From the members of the molecular repertoire of the "endometrial receptivity" period, with the exception of $\alpha_v\beta_3$, no other gene has been described thus far whose aberrant expression is associated with or results in infertility. It has been suggested that the expression of the immunoreactivity for $\alpha_4\beta_1$ and $\alpha_v\beta_3$ coincides with the putative "implantation window". Immunostaining for $\alpha_v$ increased throughout the menstrual cycle, while the $\beta_3$ subunit appeared abruptly on cycle day 20 on luminal and glandular epithelial cells. Discordant luteal phase biopsies ($\geq$3 days out of phase) from infertile patients exhibited delayed epithelial $\beta_3$ immunostaining. Later, the abnormal $\beta_3$ immunostaining was also found in infertility associated with tubal factor (Lessey et al, 1994) and unexplained infertility (Lessey et al., 1992). The data presented here, show that the molecular lesion associated with infertility is not confined to the abnormal expression of the $\beta_3$. In a substantial number of patients who are infertile, the ebaf both at the mRNA and protein level is expressed. In normal endometria, the ebaf mRNA was expressed during the premenstrual phase of the menstrual cycle. This expression continued during the menstrual bleeding. Consistent with its intimate relation to endometrial bleeding, the ebaf mRNA was also expressed in the endometria of patients with endometrial bleeding irrespective of the phase of the menstrual cycle. These findings suggest that the ebaf is expressed at the critical period of the menstrual cycle when implantation is unlikely to occur and that endometrium is destined to be shed. Therefore, premature expression of ebaf in the endometria of infertile women is likely to be a hallmark of a non-receptive endometrium. Additional studies are required to test the hypothesis whether presence or lack of ebaf in endometrium affects the outcome in the in vitro fertilization in infertile patients.

Example 5

A monoclonal and rabbit antisera were raised against the peptide CASDGALVPRRLQHRP-amide (SEQ ID NO: 3) at the COOH terminal (Tabibzadeh et al, 1998) and to acetyl-DRADMEKLVIPAC peptide (SEQ ID NO: 6) at the $NH_2$ terminal of the ebaf (FIGS. 25-26). Rabbit antiserum to CAS-DGALVPRRLQHRP-amide (SEQ ID NO: 3) was purified on a peptide column. The antibody reacted in an ELISA with the peptide (ELISA reading; 23,500) and its reactivity could be inhibited by pre-incubation of the antibody with 100 fold excess of the peptide (ELISA reading; 700). The proteins derived from endometria were subjected to Western blot analysis using this (Tabibzadeh et al, 1998) and the antibody to the $NH_2$ terminal of the ebaf. Both antibodies reacted with a 41 kD protein which is the predicted size of the precursor protein in endometrium, endometrial fluid and placenta (FIG. 25, Tabibzadeh et al, 1998). This immunoreactivity could be inhibited with excess amount of peptide and could not be seen with preimmune sera (FIG. 25A). The C-terminal antibody reacted with ~25, and ~33 kD proteins in endometrium (FIG. 25A). When the endometrial proteins were immunoprecipitated, the 12 kD protein was also detected (FIG. 25B). Using this antibody, ebaf was detected in human endometrium throughout the menstrual cycle (Tabibzadeh et al 1998). To verify the size of the ebaf protein, we transfected NIH 3T3 cell line with the sense and anti sense cDNAs of ebaf and then the cells and the conditioned media were subjected to Western blotting. The blot was probed with the affinity purified rabbit antiserum to ebaf and the monoclonal antibody to C terminal end of ebaf. As shown in FIG. 26, there was no reactivity with the cell lysates and conditioned media of cells transfected with the antisense cDNA whereas the sense cDNA induced the expression of the ebaf precursor in the cells. The conditioned media of cells transfected with sense cDNA also contained the precursor protein as well as expected mature secreted ebaf proteins in the size of ~12, ~25, and ~33 kD. These findings confirm that the ebaf exists as a precursor protein in the size of 41 kD and secreted proteins in the size of ~12, ~25, and ~33 kD (table 1) and is present in the endometrium, endometrial fluid and serum.

Throughout this application, various publications, including United States patents, are referenced by author and year and patents by number. Full citations for the publications cited are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is therefore, to be understood that within the scope of the appended claims, the invention may be practiced otherwise than as specifically described.

TABLE 1

Time Required for conception in couples who will attain pregnancy

| MONTHS OF EXPOSURE | % PREGNANCY |
|---|---|
| 3 | 57% |
| 6 | 72% |
| 12 | 85% |
| 24 | 93% |

TABLE 2

The potential cleavage sites in the ebaf and the predicted molecular weights of the released proteins

| Potential cleavage site | Number of amino acids | Predicted molecular weight (kD) |
|---|---|---|
| $1^{st}$ (RGKR) | 289 | 32.4 |
| $2^{nd}$ (RHGR) | 239 | 25.6 |
| $3^{rd}$ (RCCR) | 101 | 11.2 |

Precursor protein (40.9 kD)
NH2 terminal protein (29.7 kD) Processed protein (11.2 kD)
NH2 terminal protein (15.3 kD) Processed protein (25.6 kD)
NH2 terminal protein (8.5 kD) Processed protein (32.4 kD)

The precursor and processed proteins are shown with solid arrows. The NH2 terminal protein is shown with dashed arrows. Not drawn to scale. The predicted sizes shown does not take into account possible post-translational modification.

TABLE 3

Cases used in the Northern and Western blot analysis of TGF-β4 in the endometria of normal and infertile women

| Lane #* (Northern blot analysis) | Lane #** (Western blot analysis) | Post-ovulatory day | Condition | Result (Northern blot analysis) 2.1 kb mRNA | Result (Western blot analysis) 55-60 kD | 41-43 kD | 31-35 kD | 25-27 kD |
|---|---|---|---|---|---|---|---|---|
| 1 | 4 | 8 | Infertility, 5 years. Endometriosis, IVF failures ×2 | + | + | + | + | |
| 2 | 5 | 6 | Infertility | + | + | + | + | + |
| 3 | 6 | LP | Infertility. Endometriosis | − | + | + | + | + |
| 4 | 7 | 5 | Infertility. Endometriosis | − | + | + | + | + |
| 5 | 8 | 6 | Infertility, tubal factor | − | + | + | + | + |
| 6 | 9 | 11 | Infertility. Luteal phase defect | + | + | + | + | + |
| 7 | 10 | 12 | Infertility | − | + | + | + | + |
| 8 | ND | — | Infertility. On $E_2$/P | + | ND | ND | ND | ND |
| 9 | ND | 7 | Infertility. Hydrosalpinx | − | ND | ND | ND | ND |
| 10 | ND | 9 | Infertility, unexplained | − | ND | ND | ND | ND |
| 11 | ND | 9 | Infertility. Bilateral tubal occlusion | + | ND | ND | ND | ND |
| 12 | ND | 10 | Infertility, unexplained | + (weak) | ND | ND | ND | ND |
| 13 | 11 | 8 | Infertility, unexplained | + | + | + | + | + |
| 14 | ND | 10 | Infertility. Pelvic adhesions | + (weak) | ND | ND | ND | ND |
| 15 | ND | — | Negative control, HL60 cells | − | ND | ND | ND | ND |
| 16 | 12 | 6 | Infertility. Premature ovarian failure. Diabetes Mellitus, Sample removed in an artificial cycle. | + | + | | | |
| 17 | 13 | 12 | Infertility. Premature ovarian failure. Diabetes Mellitus, Sample removed in an artificial cycle. | + | + | + | + | + |
| 18 | 14 | 10 | Infertility. Habitual abortion.. Luteal phase defect. On clomiphene (d3-d7) | + | + | + | + | |
| 19 | 15 | 9 | Infertility, unexplained | + | + | + | | |
| 20 | 16 | LP | Infertility. Polycystic ovary. Anovulatory | − | + | + | + | + |
| 21 | 17 | 9 | Normal fertile control (egg donor) | + (weak) | − | − | − | − |
| 22 | ND | 0 | Infertility, unexplained | + | ND | ND | ND | ND |
| 23 | 18 | 6 | Infertility, unexplained | + | + | + | + | + |
| 24 | 19 | 9 | Infertility. unexplained | + | + | | + | + |
| 25 | ND | 0 | Normal fertile control (bilateral tube ligation) | + (2.1, 2.5 kb) | ND | ND | ND | ND |
| 26 | 20 | 0 | Normal fertile control (bilateral tube ligation) | + (2.1, 2.5 kb) | + | + | + | + |
| 27 | 21 | 8 | Infertility, Luteal phase defect | + (weak) | + | + | | |
| 28 | 22 | 8 | Infertility. Anovulatory | − | + | + | | |
| 29 | 23 | 8 | Infertility. Polycystic ovary | + (weak) | + | + | | |

*Lane# are those shown in FIG. 2
**Lane # are those shown in FIG. 8.
LP: Late proliferative,
ND: not done,
IVF: in vitro fertilization.

TABLE 4

Cases used for the immunohistochemical localization of the TGFβ4 in endometria.

| Case# | Cycle day | Conditions | Glands | Stroma |
|---|---|---|---|---|
| 1 | CD23 | Normal | − | − |
| 2 | CD25 | Normal | − | − |
| 3 | CD23 | Infertility. Male factor | − | − |
| 4 | CD23 | Infertility. Endometriosis | − | − |
| 5 | CD23 | Infertility. Luteal phase defect | − | − |
| 6 | CD | Infertility. Luteal phase defect. | − | − |
| 7 | CD22 | Infertility. Endometriosis | − | − |
| 9 | CD22 | Infertility. Endometriosis | − | − |
| 8 | CD22 | Habitual abortion | − | − |
| 10 | CD24 | Infertility | − | − |
| 11 | CD16 | Infertility. Endometriosis. Luteal phase defect | +++ | − |
| 12 | CD23 | Infertility, unexplained | − | + |
| 13 | CD22 | Infertility. Endometriosis | − | + |
| 14 | CD23 | Infertility. Endometriosis | − | ++ |
| 15 | CD23 | Infertility. Endometriosis | − | ++ |
| 16 | CD23 | Habitual Abortion | ++ | ++ |
| 17 | CD23 | Infertility. Endometriosis, Habitual Abortion | ++ | ++ |
| 18 | CD | Infertility. Endometriosis | +++ | ++ |
| 19 | CD22 | Infertility. Endometriosis | +++ | +++ |
| 20 | CD | Infertility, unexplained. Luteal phase defect | +++ | +++ |
| 21 | CD22 | Infertility. Endometriosis, Luteal phase defect | +++ | +++ |
| 22 | CD | Infertility.. Endometriosis. Luteal phase defect | +++ | +++ |

TABLE 5

Cases used for the Northern blot analysis

| Lane #* | Cycle day | Condition |
|---|---|---|
| 1 | 22 | Infertility, 5 years. Endometriosis, IVF Failures ×2 |
| 2 | 20 | Infertility |
| 3 | LP | Infertility. Endometriosis |
| 4 | 19 | Infertility. Endometriosis |
| 5 | 20 | Infertility, tubal |
| 6 | 25 | Infertility. Luteal phase defect |
| 7 | 26 | Infertility |
| 8 | — | Infertility. On E₂/P |
| 9 | 21 | Infertility. Hydrosalpinx |
| 10 | 23 | Infertility, unexplained |
| 11 | 23 | Infertility. Bilateral tubal occlusion |
| 12 | 24 | Infertility, unexplained |
| 13 | 22 | Infertility, unexplained |
| 14 | 24 | Infertility. Pelvic adhesions |
| 15 |  | Negative control, HL60 cells |
| 16 | 20 | Infertility. Premature ovarian failure. Diabetes Mellitus, Sample removed in an artificial cycle. |
| 17 | 26 | Infertility. Premature ovarian failure. Diabetes Mellitus, Sample removed in an artificial cycle. |
| 18 | 24 | Infertility. Habitual abortion.. Luteal phase defect. On clomiphene (d3-d7) |
| 19 | 23 | Infertility, unexplained |
| 20 | LP | Infertility. Polycystic ovary. Anovulatory |
| 21 | 23 | Egg donor |
| 22 | 0 | Infertility, unexplained |
| 23 | 20 | Infertility, unexplained |
| 24 | 23 | Infertility. unexplained |
| 25 | 0 | Normal, Bilateral tube ligation |
| 26 | 0 | Normal. Bilateral tube ligation |
| 27 | 22 | Infertility, Luteal phase defect |
| 28 | 22 | Infertility. Anovulatory |
| 29 | 22 | Infertility. Polycystic ovary |

*Lane# are those shown in FIG. 2 LP: Late proliferative

TABLE 6

Cases used for the RT-PCR-Southern blot analysis

| Lane#* | Cycle day (CD) | Negative PCR Control (-template) |
|---|---|---|
| Lane 1 | — | Negative PCR Control (-template) |
| Lane 2 | CD0 | Normal, Menstrual bleeding |
| Lane 3 | CD0 | Normal, Menstrual Bleeding |
| Lane 4 | CD23 | Normal, Egg donor |
| Lane 5 | CD22 | Infertility, Luteal phase defect |
| Lane 6 | CD20 | Infertility, unexplained |
| Lane 7 | CD23 | Infertility, unexplained Nulliparous |
| Lane 8 | CD18 | Infertility, unexplained, Failed IVF and GIFT |
| Lane 9 | CD20 | Infertility, unexplained |
| Lane 10 | CD20 | Infertility, Luteal phase defect |
| Lane 11 | CD22 | Infertility, Polycystic ovary |
| Lane 12 | CD22 | Infertility, unexplained |
| Lane 13 | CD20 | Infertility, Polycystic ovary |
| Lane 14 | CD21 | Infertility, unexplained. Hydrosalpinx. Endo Factor? |
| Lane 15 | CD22 | Infertility, Anovulatory |
| Lane 16 | CD22 | Infertility, Unexplained Endometriosis |
| Lane 17 | CD26 | Infertility, Premature Ovarian Failure |
| Lane 18 | CD23 | Unexplained infertility |

*Lane#s are those shown in FIG. 2

TABLE 7

Cases used for the immunohistochemical localization of the TGFβ4 in endometrial.

| Case# | Cycle day | Conditions | Glands | Stroma |
|---|---|---|---|---|
| 1 | CD23 | Normal | − | − |
| 2 | CD25 | Normal | − | − |
| 3 | CD23 | Infertility, Male factor | − | − |
| 4 | CD23 | Infertility, Endometriosis | − | − |
| 5 | CD23 | Infertility, Luteal phase defect | − | − |
| 6 | CD | Infertility, Luteal phase defect | − | − |
| 7 | CD22 | Infertility, Endometriosis | − | − |
| 9 | CD22 | Infertility, Endometriosis | − | − |
| 8 | CD22 | Habitual abortion | − | − |
| 10 | CD24 | Infertility | − | − |
| 11 | CD16 | Infertility, Endometriosis Luteal phase defect | +++ | − |
| 12 | CD23 | Infertility, unexplained | − | + |
| 13 | CD22 | Infertility, Endometriosis | − | + |
| 14 | CD23 | Infertility, Endometriosis | − | ++ |
| 15 | CD23 | Infertility, Endometriosis | − | ++ |
| 16 | CD23 | Habitual abortion | ++ | ++ |
| 17 | CD23 | Infertility, Endometriosis, Habitual abortion | ++ | ++ |
| 18 | CD | Infertility, Endometriosis | +++ | ++ |
| 19 | CD22 | Infertility, Endometriosis | +++ | +++ |
| 20 | CD | Infertility, unexplained Luteal phase defect | +++ | +++ |
| 21 | CD22 | Infertility, Endometriosis, Luteal phase defect | +++ | +++ |
| 22 | CD | Infertility, Endometriosis, Luteal phase defect | +++ | +++ |

REFERENCES

Armant D. R., Kaplan H. A., Lennarz W. J., 1986.
Arcici A., Engin O., Attar E., Olive D. L., 1995.
Axelrod H. R., 1985.
Baird D. D., Weinberg C. R., Wilcox A. J., McConnaughey D. R., Musey P. I., Collins D. C., 1991.
Behrendtsen O., Alexander C. M., Werb Z., 1992.
Belin D., Wohlwend A., Schleuning W. D., Kruithof E K., Vassalli J. D., 1989.
Bouillet P., Qulad-Abdelghani M., Vicaire S., et al., 1995.
Boyd J. D., Hamilton W. J., 1967.
Braga V. M. Gendler S. J., 1993.

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251-270 (1991).

Capecchi, "Altering the genome by homologous recombination" *Science* 244:1288-1292 (1989).

Carmeliet P., Schoonjans L., Kieckens L., Ream B., Degen J., Bronson R., De Vos R., van den Oord J. J., Collen D., Mulligan R. C., 1994.

Carson D. D., Tang J-P., Julian J., 1993.

Chard T., 1991.

Chomczynski P. and Sacchi N., 1987.

Cregg J M, Vedvick T S, Raschke W C: Recent Advances in the Expression of Foreign Genes in *Pichia pastoris*, Bio/Technology 11:905-910, 1993.

Culver, 1998. Site-Directed recombination for repair of mutations in the human ADA gene. (Abstract) Antisense DNA & RNA based therapeutics, February, 1998, Coronado, Calif.

Cowell T. P., 1969.

Cross J. C., Werb Z., Fisher S. J., 1994.

Dahlen J. R., Jean F., Thomas G., Foster D. C., Kisiel W., 1998.

Dand W., Polan M. L., 1994.

Dano K., Andreasen J., Grondahl-Hansen, Kristensen P., Nielsen L. S., Skriver, 1985.

Daopin S., Piez K. A., Ogawa Y., Davies D. R., 1992.

Das S. K., Wang X-N., Paria B. C., Damm D., Abraham J. A., Klagsbrun M., Klagsbrun M., Andrews G. K., Dey S. K., 1994.

Davies et al., "Targeted alterations in yeast artificial chromosomes for inter-species gene transfer", *Nucleic Acids Research*, Vol. 20, No. 11, pp. 2693-2698 (1992).

Denker H. W., Fritz H., 1979.

Denker H. W., 1993.

Dickinson et al., "High frequency gene targeting using insertional vectors", *Human Molecular Genetics*, Vol. 2, No. 8, pp. 1299-1302 (1993).

Ding Y-X, Zhu L. J., Bagchi M. K., Bagchi I. C., 1994.

Duff and Lincoln, "Insertion of a pathogenic mutation into a yeast artificial chromosome containing the human APP gene and expression in ES cells", *Research Advances in Alzheimer's Disease and Related Disorders*, 1995.

Estreicher A., Muhlhauser J., Carpentier J., Orci J-L, Vassali J-D., 1990.

Finn C. A., 1973.

Fisher S. J., Cui T., Zhang L., Hartman L., Grahl K., Guo-Yang Z., Tarpey J., Damsky C., 1989.

Formigli L. G., Formigli C., Roccio C., 1987.

Fukuda M. N., Sato T., Nakayama J., Klier G., Mikami M., Aoki D., Nozawa S., 1995.

Garcia J. E., Acosta A. A., Hsiu J. G., Jones Jr. H. W., 1984.

Gilboa, E, Eglitis, M A, Kantoff, P W, Anderson, W F: Transfer and expression of cloned genes using retroviral vectors. BioTechniques 4(6):504-512, 1986.

Glass R. H., Aggeler J., Spindle A. I., Pedersen R. A., Web A., 1983.

Graham C. H., Lala P. K., 1991.

Graham C. H., Lala P. K., 1992a.

Graham C. H., Lysiak J. J., McCrae K. R., Lala P. K., 1992b.

Guttmacher A F: Factors affecting normal expectancy of conception. (1956) *JAMA* 16, 855-864.

Guzick D. S., 1989.

Hertig A., 1956.

Hampton A. L., Salamonsen L. A., 1994.

Herz J., Clouthier D. E., Nakker R. E., 1992.

Hey N. A., Graham R. A., Seif M. W., Aplin J. D., 1994.

Hsu S. M., Raine L., Fanger H., 1981.

Huston et al, 1991 "Protein engineering of single-chain Fv analogs and fusion proteins" in Methods in Enzymology (J J Langone, ed.; Academic Press, New York, N.Y.) 203:46-88.

Huxley et al., "The human HPRT gene on a yeast artificial chromosome is functional when transferred to mouse cells by cell fusion", *Genomics*, 9:742-750 (1991).

Hynes R. O., 1987.

Jakobovits et al., "Germ-line transmission and expression of a human-derived yeast artificial chromosome", *Nature*, Vol. 362, pp. 255-261 (1993).

Jiang W., Bond J. S., 1992.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88-99.

Jones C. M., Simon-Chazottes D., Guenet J-L., Hogan B. L. M., 1992.

Kingsley D. M., 1994.

Kirby D. R. S., 1960.

Kirby D. R. S., 1963a.

Kirby D. R. S., 1962b.

Kirby D. R. S., 1965.

Klentzeris L. D., Bulmer J. N., Trejdosiewicz L. K., Morrison L., Cooke I. D., 1994.

Korach K. S., 1994.

Kothapalli R., Buyuksal, I., Wu S. Q., et al., 1997.

Kristensen T., Moestrup S. K., Gliemann J., Bendtsen L., Sane O., Sottrup-Jensen L., 1990.

Laemmeli U. K., 1970.

Laiho M., Keski-Oja J., 1989.

Lala P. K., Yagel S., Parhar R. S., Graham C. H., 1989.

Lamb et al., "Introduction and expression of the 400 kilobase precursor amyloid protein gene in transgenic mice", *Nature Genetics*, Vol. 5, pp. 22-29 (1993).

Lessey B. A., Danjanovich L., Coutfaris C., Castelbaum A., Albelda S. M., Buck C. A., 1992.

Lessey B. A., Castelbaum A. J., Buck C. A., Lei Y., Yowell C. W., Sun J., 1994.

Lessey B. A., Castelbaum A. J., Sawin S. W., Sun J., 1995.

Lessing J. B., Kraicer P. F., 1996.

Librach C. L., Web Z., Fitzgerald M. L., Chiu K., Corwin N. M., Esteves R. A., Grobelny D., Galardy R., Damsky C. H., Fisher S. J., 1991.

Loke Y. W., 1990.

Loskutoff D. J. Sawdey M., Mirmuro J., 1989.

Lydon J. P., DeMayo F. J., Conneely O. M., O'Malley B. W., 1996.

Lyons R. M., Keski-Oja J., Moses H. L., 1988.

Martel D., Frydman R., Glissant M., Maggioni C., Roche D., Psychoyos A., 1987.

Massague J., 1990.

McDonald N. Q. and Hendrickson W. A., 1993.

McPherron A. and Lee S. J., 1993.

Meno C., Saijoh Y., Fujii H., et al., 1996.

Mernaugh and Mernaugh, 1995 "An overview of phage-displayed recombinant antibodies" in Molecular Methods In Plant Pathology (RP Singh and US Singh, eds.; CRC Press Inc., Boca Raton, Fla.) pp. 359-365.

Meyer W. R., Castelbaum A. J., Somkuti S., Sagoskin A. W., Doyle M., Harris J. E., Lessey A. B., 1997.

Miller M. A., 1993.

Molloy S. S., Bresnahan P. A., Leppla S. H., Klimpel K. R., Thomas, 1992.

Mosher W. D., Pratt W. F., 1991.
Mosher W. D., Pratt W. F., 1993.
Murphy G., Atkinson S., Ward R., Gavrilovic J., Reynolds J. J., 1992.
Navot D., Laufer N., Kopolovic J., Rabinowitz R., Birkenfeld A., Lewin A., Granat M., Margalioth E. J., Schenaker J. G., 1986.
Navot D. M., Anderson T. L., Droesh K., Scott R. T., Kreiner D., Kreiner Z., Rosenwaks Z., 1989.
Navot D. M., Scott R. T., Droesh K., Kreiner D., Veeck L. L., Liu H. C., Rosenwaks Z., (1991).
Noyes R. W. and Hertig A. T., 1950.
Hykjaer A., Peterson C. M., Moller B., Jensen P. H., Moestrup S. K., Holtet T. L., Etzerodt M., Thogersen H. C., Much M., Andreasen P. A., Gliemann J., 1992.
Orth K., Madison E. L., Gething M-J., Sambrook J. F., Herz J., 1992.
Panoskaltsis-Mortari A., 1995.
Pearson and Choi, Expression of the human b-amyloid precursor protein gene from a yeast artificial chromosome in transgenic mice. Proc. Natl. Scad. Sci. USA, 1993.
Pollard J. W., Hunt J. S., Wiktor-Jedrejczak w., Stanley E. R., 1991.
Psychoyos A., 1973a.
Psychoyos A., 1973b.
Psychoyos A., Casmiri V., 1980.
Psychoyos A., 1986.
Psychoyos A., 1993.
Queenan J. T., Kao L-C., Arboleda C. E., Ulloa-Aguirre A., Gaolos T. G., Cines D. B., Strauss J. F., 1987.
Rappopolee D. A., Mark D., Banda M. J., Werb Z., 1988.
Reif A. E. and Allen J. M., 1966.
Repesh L. A., 1989.
Rogers P. A. W., Murphy C. R., 1989.
Rodgers W. H., Matrisian L. M., Giudice L. C., Dsupin B., Cannon P., Svitek C., Gorstein F., Osteen K. G., 1994.
Roldan A., Cubellis M. V., Massucci M. T., Behrendt N., Lund L. R., Dano K., Appella E., Blasi F., 1990.
Rosenwak Z., 1987.
Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281-301 (1991).
Ruoslahti E., Pierschbacher M. D., 1987.
Ruoslahti E., 1991.
Ryan I. P. and Taylor R. N., 1997.
Sambrook J., Fritsch E. F., Maniatis T., 1989.
Sanger F., Nicklen S., Coulson A. R., 1977.
Sato Y., Rifkin D. B., 1989.
Schedl et al., "A yeast artificial chromosome covering the tyrosinase gene confers copy number-dependent expression in transgenic mice", *Nature*, Vol. 362, pp. 258-261 (1993).
Schlafke S, and Enders A. C., 1975.
Shimonovitz S., Hurwitz A., Dushnik M., Anteby E., Geva-Eldar T., Simcha Y., 1994.
Speroff L., Glass R. H., Kase N. G., 1994.
Stewart C. L., Kaspar P., Brunet L. J., Bhatt H., Gadil I., Kontgen F., Abbondanzo S. J., 1992.
Strauss J. F., Gurpide E., 1991.
Strauss et al., "Germ line transmission of a yeast artificial chromosome spanning the murine $a_1$ (I) collagen locus", *Science*, Vol. 259, pp. 1904-1907 (1993).
Strickland S., Reich E., Sherman M. I., 1976.
Suminami Y., Kishi F., Sekiguchi K., Kato H., 1991.
Sutherland A. E., Calarco P. G., Damsky C. H., 1993.
Tabibzadeh S. and Satyaswaroop P. G., 1988.
Tabibzadeh S., Santhanam U., Sehgal P. B. and May L., 1989.
Tabibzadeh S., Kong Q. F., Babaknia A., May L. T., 1995.
Tabibzadeh S., 1995.
Tabibzadeh S, and Babaknia A., 1995.
Tabibzadeh S., Kong Q. F., Babaknia A., 1996.
Tabibzadeh S., 1996.
Tabibzadeh S., Kothapalli R., Buyuksai I., 1997.
Tur-Kaspa I., Confino E., Dudkiewicz A. B., Myers S. A., Friberg J., Gleihcer N., 1990.
Valdizan M. C., Julian J., Cardon D. D., 1992.
Waterhouse P., Denhardt D. T., Khokha R., 1993.
Wilcox A. J., Weinberg C. R., Wehmann R. E., Armstrong E. G., Canfield R. E., Nisula B. C., 1985.
Woessner J. F., 1991.
Ye, R. D., Ahern S. M., Le Beau M. M., Lebo R. V., Sadler J. E., 1989.
Zini J-M., Murray S. C., Graham C. H., Lala P. K., Kariko K., Barnathan E. S., Mazar A., Kerkin J., Cines D. B., McCrae K. R., 1992.
M Gruidl, A Buyuksal, A Babaknia, A T Fazleabas, S Sivarajah, P G Satyaswaroop, S Tabibzadeh: The progressive rise in the expression of a crystallin B chain in human endometrium is initiated during the implantation window; Modulation of gene expression by steroid hormones. Mol Hum Reprod 3, 333-342, 1997.
Lessey B A, Castelbaum A J, Buck C A, Lei Y, Yowell C W, Sun J: Further characterization of endometrial integrins during the menstrual cycle and in pregnancy. Fertil Steril 62, 497-506, 1994
Lessey B A, Danjanovich L, Coutfaris C, Castelbaum A, Albelda S M, Buck C A: Integrin adhesion molecules in the human endometrium. Correlation with the normal and abnormal menstrual cycle. J Clin Invest 90, 188-195, 1992)
Kumar S, Zhu L J, Polihronis M, Cameron S T, Baird D T, Schatz F, Dua A, Ying Y K, Bagchi M K, Bagchi I C: Progesterone induces calcitonin gene expression in human endometrium within the putative window of implantation. J Clin Endocrinol Metab 1998 December; 83(12):4443-50.
Molloy S S, Anderson E D, Jean, Thomas Gary: Bi-cycling the furin pathway from TGN localization to pathogen activation and embryogenesis. Trends Cell Biol 9: 28-35, 1999

We claim:

1. A contraceptive composition comprising an effective amount of a human ebaf protein in a pharmaceutically-acceptable carrier, wherein the human ebaf has a molecular weight of about 41 kD and comprises the amino acid sequence shown in SEQ ID NO: 3, and wherein the composition comprises one or more fragments of human ebaf protein wherein the fragment of human ebaf protein has a molecular weight of about 33 kD, 25 kD, or 12 kD, and wherein the composition is provided in a contraceptive device.

2. The contraceptive composition according to claim 1, wherein the composition is provided in a form for oral or parenteral administration.

3. The contraceptive composition according to claim 1, wherein the composition is provided in implant form.

4. The contraceptive composition according to claim 1, wherein the composition comprises a fragment of human ebaf protein having a molecular weight of about 33 kD.

5. The contraceptive composition according claim 1, wherein the composition comprises a fragment of human ebaf protein having a molecular weight of about 25 kD.

6. The contraceptive composition according to claim 1, wherein the composition comprises a fragment of human ebaf protein having a molecular weight of about 12 kD.

7. A method for preventing pregnancy in a female animal, comprising administering to the female animal an effective amount of a contraceptive composition comprising an effective amount of a protein an human ebaf protein in a pharmaceutically-acceptable carrier, wherein the human ebaf protein has a molecular weight of about 41 kD and comprises the amino acid sequence shown in SEQ ID NO: 3, and wherein the composition comprises one or more fragments of human ebaf protein wherein the fragment of human ebaf protein has a molecular weight of about 33 kD, 25 kD, or 12 kD, and wherein the composition is provided in a contraceptive device.

8. The method according to claim 7, wherein the female animal is human.

9. The method according to claim 7, wherein the composition is administered orally or parenterally.

10. The method according to claim 7, wherein the composition is administered as an implant.

11. The method according to claim 7, wherein the composition comprises a fragment of human ebaf protein having a molecular weight of about 33 kD.

12. The method according to claim 7, wherein the composition comprises a fragment of human ebaf protein having a molecular weight of about 25 kD.

13. The method according to claim 7, wherein the composition comprises a fragment of human ebaf protein having a molecular weight of about 12 kD.

* * * * *

UNITED STATES PATENT AND TRADEMARK OFFICE
CERTIFICATE OF CORRECTION

PATENT NO. : 8,106,001 B2
APPLICATION NO. : 11/796404
DATED : January 31, 2012
INVENTOR(S) : Siamak Tabibzadeh et al.

Page 1 of 1

It is certified that error appears in the above-identified patent and that said Letters Patent is hereby corrected as shown below:

Column 8,
Line 25, "SR) ID NO:" should read --(SEQ ID NO:--.
Line 16, "(55/60," should read --(~55/60,--.

Column 16,
Line 25, "the is expression" should read --the expression--.

Column 29,
Line 52, "with Sequences" should read --with Sequenase--.
Line 60, "at 6.5°C" should read --at 65° C--.

Column 30,
Line 15, "KG," should read --KCl,--.

Column 45,
Line 50, "ebaf has" should read --ebaf protein has--.

Column 46,
Line 53, "of a protein an human" should read --of a human--.

Signed and Sealed this
Eighth Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,106,001 B2
APPLICATION NO. : 11/796404
DATED : January 31, 2012
INVENTOR(S) : Siamak Tabibzadeh et al.

It is certified that error appears in the above-identified patent and that said Letters Patent is hereby corrected as shown below:

In the Specifications:

Column 1,
Lines 23-26,
"Grant Number (s) CA46866 awarded by the National Institutes of Health (NIH) and HD 35041 and HD 34824 from the National Cooperative Program on Markers of Uterine receptivity for Blastocyst Implantation."

should read

--Grant Numbers CA46866, HD 35041, and HD 34824 awarded by the National Institutes of Health (NIH).--

Signed and Sealed this
Fourteenth Day of May, 2013

Teresa Stanek Rea
*Acting Director of the United States Patent and Trademark Office*

SEQUENCE LISTING

<160> NUMBER OF SEQ ID NOS: 6

<210> SEQ ID NO 1
<211> LENGTH: 1962
<212> TYPE: DNA
<213> ORGANISM: homo sapien

<400> SEQUENCE: 1

```
ccccactctg cctcctgctc ccccagggca gcaccatgtg gccccgtgtgg ctctgctggg      60 cactctgggt gctgcccctg gctggcccg gggcggccct gaccgaggag cagctcctgg       120
cgagcctgct gcggcagctg cagctcagcg aggtgcccgt actggacagg ccgacatgg       180 agaagctggt catccccgcc cacgtgaggg cccagtatgt agtcctgctg cggcgcgacg      240
gggaccgctc ccgcggaaag aggttcagcc agagcttccg agaggtggcc ggcaggttcc      300
tggcgtcgga ggccagcaca cacctgctgg tgttcggcat ggagcagcgg ctgccgccca      360
acagcgagct ggtgcaggcc gtgctgcggc tcttccagga gccggttccc caaggcgcgc      420
tgcacaggca cgggcggctg tccccggcag cgcccaaggc ccgggtgacc gtcgagtggc      480
tggtccgcga cgacggctcc aaccgcacct ccctcatcga ctccaggctg gtgtccgtcc      540
acgagagcgg ctggaaggcc ttcgacgtga ccgaggccgt gaacttctgg cagcagctga      600
gccggccccc ggagccgctg ctcgtacagg tgtcggtgca gagggagcat ctgggcccgc      660
tggcgtccgg cgcccacaag ctggtccgct ttgcctcgca gggggcgcca gccgggcttg      720
gggagcccca gctggagctg cacaccctgg acctcaggga ctatggagct cagggcgact      780
gtgaccctga agcaccaatg accgagggca cccgctgctg ccgccaggag atgtacattg      840
acctgcaggg gatgaagtgg gccaagaact gggtgctgga gccccgggc ttcctggctt       900 acgagtgtgt gggcacctgc cagcagcccc cggaagccct ggccttcaat tggccatttc      960
tggggccgcg acagtgtatc gcctcggaga ctgcctcgct gcccatgatc gtcagcatca      1020
aggagggagg caggaccagg ccccaggtgg tcagcctgcc caacatgagg gtgcagaagt      1080
gcagctgtgc ctcggatggg gcgctcgtgc caaggaggct ccagcatagg ccctggtgta      1140
tccattgagc ctctaactga acgtgtgcat aagaggtggc ttaatgtag ggcgttaact       1200 ttatacttag caagttactc catcccaatt tagtgctcct gtgtgacctc gccctgtgtc      1260
cttccattcc tgtctttccc gtccatcacc catcctaagc acttacgtga gtaaataatg      1320
cagctcagat gctgagctct agtaggaaat gctggcatgc tgattacaag atacagctga      1380
gcaatgcaca cattttcagc tgggagtttc tgttctctgg caaattcttc actgagtctg      1440
gaacaataat accctatgat tagaactggg gaaacagaac tgaattgctg tgttatatga      1500
ggaattaaaa ccttcaaatc tctatttccc ccaaatactg acccattctg gacttttgta     1560
aacataccta ggcccctgtt cccctgagag ggtgctaaga ggaaggatga gggcttcagg     1620 ctggggggcag tggacaggga attgggatac ctggattctg gttctgacag ggccacaagc    1680
taggatctct aacaaacgca gaaggctttg gctcgtcatt tcctcttaaa aaaggaggag     1740
ctgggcttca gctctaagaa cttcattgcc ctggggatca gacagcccct acctaccct     1800 gcccactcct ctggagactg agccttgccc gtgcatattt aggtcattc ccacactgtc      1860 ttagagaact tgtcaccaga aaccacatgt atttgcatgt tttttgttaa tttagctaaa     1920
gcaattgaat gtagatactc agaagaaata aaaaatgatg tt                        1962
```

<210> SEQ ID NO 2
<211> LENGTH: 4
<212> TYPE: PRT
<213> ORGANISM: artificial sequence
<220> FEATURE:
<221> NAME/KEY: artificial sequence
<222> LOCATION: (1)..(4)
<223> OTHER INFORMATION: pre-pro-protein cleavage site where X is any
      amino acid

<400> SEQUENCE: 2

```
-continued

Arg Xaa Xaa Arg
1

<210> SEQ ID NO 3
<211> LENGTH: 16
<212> TYPE: PRT
<213> ORGANISM: homo sapien

<400> SEQUENCE: 3

Cys Ala Ser Asp Gly Ala Leu Val Pro Arg Arg Leu Gln His Arg Pro
1               5                   10                  15

<210> SEQ ID NO 4
<211> LENGTH: 19
<212> TYPE: DNA
<213> ORGANISM: artificial sequence
<220> FEATURE:
<221> NAME/KEY: artificial sequence
<222> LOCATION: (1)..(19)
<223> OTHER INFORMATION: 5' primer

<400> SEQUENCE: 4
tcagcgaggt gcccgtact                                            19

<210> SEQ ID NO 5
<211> LENGTH: 19
<212> TYPE: DNA
<213> ORGANISM: artificial sequence
<220> FEATURE:
<221> NAME/KEY: artificial sequence
<222> LOCATION: (1)..(19)
<223> OTHER INFORMATION: 3' primer

<400> SEQUENCE: 5
agttcttaga gctgaagcc                                            19

<210> SEQ ID NO 6
<211> LENGTH: 13
<212> TYPE: PRT
<213> ORGANISM: homo sapien

<400> SEQUENCE: 6

Asp Arg Ala Asp Met Glu Lys Leu Val Ile Pro Ala Cys
1               5                   10
```